United States Patent
Mastalerz et al.

(10) Patent No.: US 6,908,916 B2
(45) Date of Patent: Jun. 21, 2005

(54) C-5 MODIFIED INDAZOLYLPYRROLOTRIAZINES

(75) Inventors: Harold Mastalerz, Guilford, CT (US);
Guifen Zhang, Wallingford, CT (US);
James G. Tarrant, Hamden, CT (US);
Gregory D. Vite, Titusville, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 141 days.

(21) Appl. No.: 10/294,281

(22) Filed: Nov. 14, 2002

(65) Prior Publication Data

US 2003/0186983 A1 Oct. 2, 2003

Related U.S. Application Data

(60) Provisional application No. 60/333,014, filed on Nov. 14, 2001.

(51) Int. Cl.$^7$ ..................... C07D 403/12; A61K 31/416
(52) U.S. Cl. .................... 514/218; 514/233.2; 514/243; 514/228.5; 540/492; 540/575; 544/61; 544/62; 544/112; 544/183
(58) Field of Search ............................ 544/61, 62, 112, 544/183; 540/492, 575; 514/218, 228.5, 233.2, 243

(56) References Cited

U.S. PATENT DOCUMENTS 4,908,056 A 3/1990 Tseng .............................. 71/90

FOREIGN PATENT DOCUMENTS

| EP | 778 277 A1 | 6/1997 |
| WO | WO 98/08847 | 3/1998 |
| WO | WO 01/14378 | 1/2001 |

OTHER PUBLICATIONS

Simone, Oncology: Introduction, Cecil Textbook of Medicine, 20$^{th}$ Edition, vol. 1, pp. 1004–1010, 1996.*
Traxler, Protein Tyrosine Kinase inhibitors in cancer treatment, Exp. Opin. Ther. Patents, 7(6):571–588, 1997.*
Marmor et al., Signal Transduction and Oncogenesis by ErbB/HER Receptors, Int. J. Radiation Oncology Biol. Phys., vol. 58, No. 3, pp. 903–913, 2004.*
Otter et al, Nucleoside & Nucleotides, 15(1–3), 793–807 (1996).
Quintela et al, Tetrahedron, 52(8), 3037–3048 (1996).
Patil et al, J. Heterocyclic Chem., 31(4), 781–807 (1994).
Neunhoeffer et al, Justus Liebigs Ann. Chem., vol. 9, 1413–1420 (1977) & Chem. Abstr. 88:121113q, (Apr. 1978).
Skobe et al, Nature Medicine, vol. 3, No. 11, 1223–1227 (Nov. 1997).

* cited by examiner

*Primary Examiner*—Deepak Rao
(74) *Attorney, Agent, or Firm*—Elliott Korsen; Kenneth Peist

(57) ABSTRACT

The present invention provides compounds of formula I

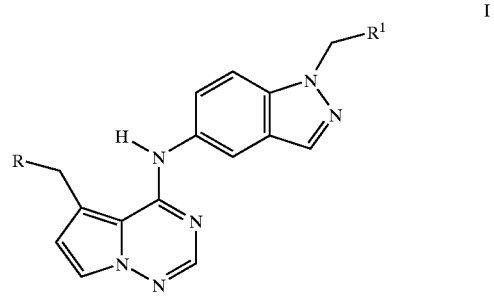

and pharmaceutically acceptable salts thereof.

The formula I compounds inhibit tyrosine kinase activity of growth factor receptors such as HER1, HER2 and HER4 thereby making them useful as antiproliferative agents. The formula I compounds are also useful for the treatment of other diseases associated with signal transduction pathways operating through growth factor receptors.

9 Claims, No Drawings

C-5 MODIFIED INDAZOLYLPYRROLOTRIAZINES

This application claims a benefit of priority from U.S. application Ser. No. 60/333,014 filed Nov. 14, 2001, the entire disclosure of which is herein incorporated by reference.

FIELD OF THE INVENTION

This invention relates to compounds that inhibit the tyrosine kinase activity of growth factor receptors such as HER1, HER2, and HER4 thereby making them useful as anti-cancer agents. The compounds are also useful in the treatment of diseases, other than cancer, which are associated with signal transduction pathways operating through growth factor receptors such as HER1, HER2 and HER4.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3, and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

SUMMARY

The compounds of the invention inhibit the tyrosine kinase activity of growth factor receptors such as HER 1, HER2, and HER4 and as such, can be used to treat diseases that are associated with signal transduction pathways operating through growth factor receptors. For example the compounds of the instant invention can be used as antiproliferatives and anticancer agents. More specifically, the invention comprises a compound of formula I

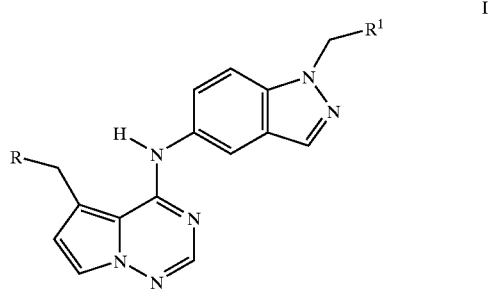

I its enantiomers, diastereomers, and pharmaceutically acceptable salts, prodrugs and solvates thereof, wherein R is selected from the group consisting of $SR^2$, $SOR^2$, $SO_2R^2$, $OR^2$, and $NR^3R^4$; $R^1$ is selected from the group consisting of aryl, substituted aryl, heterocyclo, and substituted heterocyclo; $R^2$ is selected from the group consisting of hydrogen, alkyl, substituted alkyl, aryl, substituted aryl, aralkyl, heterocyclo, and substituted heterocyclo; $R^3$ and $R^4$ are independently selected from the group consisting of hydrogen, alkyl, substituted alkyl, aryl, substituted aryl, heterocyclo, and substituted heterocyclo; or $R^3$ and $R^4$ may together form an optionally substituted monocyclic 4–8 membered saturated or unsaturated carbocyclic or heterocyclic ring, or an optionally substituted bicyclic 7–12 membered saturated or unsaturated carbocyclic or heterocyclic ring.

Also provided for is a method for treating proliferative diseases, comprising administering to a warm-blooded species in need thereof, a therapeutically effective amount of a compound of formula I.

DESCRIPTION

The present invention provides for compounds of formula I, pharmaceutical compositions employing such compounds and for methods of using such compounds.

In accordance with the present invention, compounds of formula I

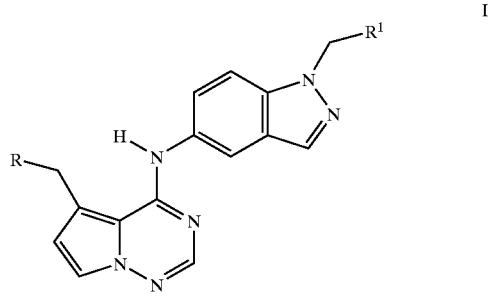

I their enantiomers, diastereomers, and pharmaceutically acceptable salts, prodrugs and solvates thereof inhibit the tyrosine kinase activity of growth factor receptors such as HER2. In formula I and throughout the specification, the above symbols are defined as follows:

R is selected from $SR^2$, $SOR^2$, $SO_2R^2$, $OR^2$, $NR^3R^4$;

$R^1$ is aryl, substituted aryl, heterocyclo, substituted heterocyclo;

$R^2$ is hydrogen, alkyl, substituted alkyl, aryl, substituted aryl, aralkyl, heterocyclo, substituted heterocyclo;

$R^3$ and $R^4$ are independently hydrogen, alkyl, substituted alkyl, aryl, substituted aryl, heterocyclo, or substituted heterocyclo or $R^2$ and $R^3$ may together form an optionally substituted monocyclic 4–8 membered saturated or unsaturated carbocyclic or heterocyclic ring, or an optionally substituted bicyclic 7–12 membered saturated or unsaturated carbocyclic or heterocyclic ring;

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclo, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclo. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocyclos, such as, epoxides and aziridines.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

It should further be understood that solvates (e.g., hydrates) of the compounds of formula I are also with the scope of the present invention. Methods of solvation are generally known in the art.

In a preferred embodiment, the invention comprises a compound of formula II,

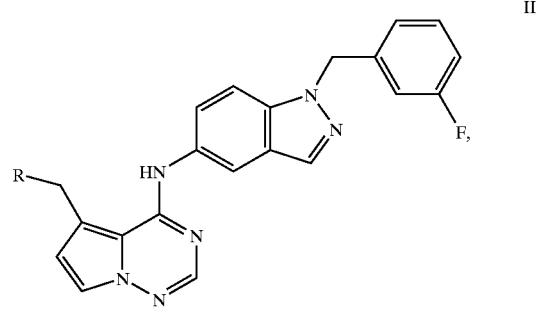

its enantiomers, diastereomers, and pharmaceutically acceptable salts, prodrugs and solvates thereof, wherein R is the same as previously defined above.

In yet another preferred embodiment, the invention comprises a compound of formula III

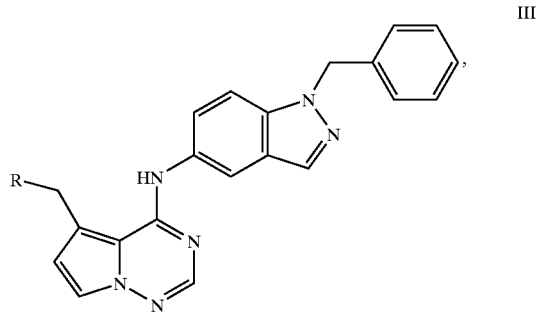

its enantiomers, diastereomers, and pharmaceutically acceptable salts, prodrugs and solvates thereof, wherein R is the same as previously defined above.

In still yet another embodiment, the invention comprises a compound a formula IV,

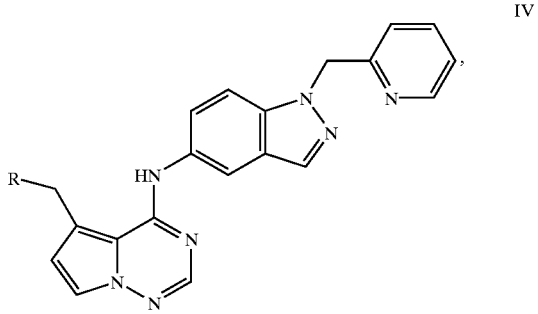

its enantiomers, diastereomers, and pharmaceutically acceptable salts, prodrugs and solvates thereof, wherein R is the same as previously defined above.

Use and Utility

The present invention is based on the discovery that certain pyrrolotriazines are inhibitors of protein kinases. More specifically, pyrrolotriazines such as those described in this invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, oesophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of non-cancerous disorders such as psoriasis and rheumatoid arthritis.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit HER1, HER2, and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor effficacy in preclincal and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agens such as Taxol, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as anti-angiogenic agents. See the following documents and references cited therein: Schlessinger J., "Cell signaling by receptor tyrosine kinases", *Cell* 103(2), p. 211–225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000); Satoh, K., Kikuchi, S., Sekimata, M., Kabuyama, Y., Homma, M. K., and Homma Y., "Involvement of ErbB-2 in rheumatoid synovial cell growth", *Arthritis Rheum.* 44(2), p. 260–265 (2001).

The antiproliferative treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative treatment defined herein before may be:

surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxin);

(ii) cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), anti-neoplastic harmonal agents, antiprogestogens, antiandrogens (for example flutamide, nilutamide, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of other growth factor function, (such growth factors include for example FGF, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like taxol, taxotere and newer microbtubule agents such as epothilone analogs, discodermolide analogs, and eleutherobin analogs);

topoisomerase inhibitors (for example epipodophyllotoxins like etoposide and teniposide, amsacrine, topotecan); cell cycle inhibitors (for example flavopyridols); and biological response modifiers.

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, and osteosarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 200 mg/kg/day, preferably less than 100 mg/kg/day, in a single dose or in 2 to 4 divided doses.

Biological Assays

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 µM ATP, and 4 µCi/ml [$\gamma$-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with $IC_{50}$ values between 0.001 25 µM. Preferred compounds have $IC_{50}$ values between 0.001–5.0 µM. More preferred compounds have $IC_{50}$ values between 0.001–1.0 µM. Most preferred compounds have $IC_{50}$ values between 0.001–0.1 µM.

A HERG potassium channel assay may be used to screen compounds for HERG activity (see Caballero R, et al., *Direct Effects of Candesartan and Eprosartan on Human Cloned Potassium Channels Involved in Cardiac Repolarization*, Molecular Pharmacology, Vol. 59, No. 4, pp.

825–36, 2001). Accordingly, preferred compounds have lower HERG assay activity.

Methods of Preparation

Certain compounds of formula I may generally be prepared according to the following schemes and the knowledge of one skilled in the art. Supplemental preparation information may also be found in co-pending U.S. patent application Ser. No. 09/573,829 filed May 18, 2000 and international application published under the Patent Cooperation Treaty (PCT), International Publication Number WO 00/71129, both herein incorporated by reference.

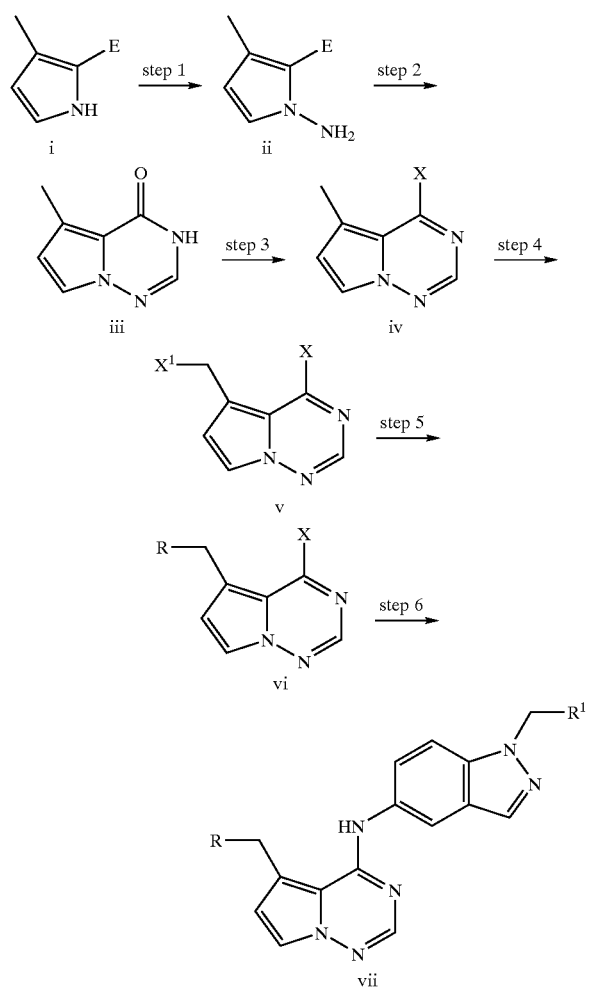

wherein E is an ester group and X and X¹ are halogen

Step 1

The first step of Scheme 1 is accomplished by treatment of a 3-methyl-1H-pyrrole-2-carboxylic acid ester i (T. D. Lash et al., J. Heterocyclic Chem., 1991, 28, 1671) with a base such as potassium t-butoxide or sodium hydride in an anhydrous solvent such as THF or DMF followed by an aminating reagent, such as O-(2,4-dinitro-phenyl)-hydroxylamine (T. Sheradsky, J. Heterocyclic Chem., 1967, 4, 413) or chloramine (I. P. Sword, J. Chem. Soc. C, 1971, 820) to give the pyrrolylamine ii.

Step 2

The pyrrolylamine ii is heated with excess formamide to give the pyrrolotriazinone iii.

Step 3

Compound iii is converted to a 4-halo-pyrrolotriazine iv by heating with the appropriate phosphorus oxyhalide, e.g., the 4-chloro-pyrrolotriazine is obtained by heating iii with phosphorus oxychloride.

Step 4

Halogenation of the 5-methyl group of iv is affected by treatment with a halogenating agent such as a N-bromosuccinimide or sulfuryl chloride. The reaction is performed under an inert atmosphere such as $N_2$ in the presence of a catalyst such as dibenzoyl peroxide or 2,2'-azobisisobutyronitrile, or irradiation and gives the 4-halo-5-halomethyl-pyrrolotriazine v.

Step 5

Treatment of v with a thiol, a thiocarboxylic acid, water, an alcohol, a carboxylic acid, a primary or a secondary amine in the presence of a base such as $NaHCO_3$ or triethylamine in a solvent such as acetonitrile affords intermediate vi in Scheme 1.

Step 6

Treatment of vi with a 5-amino-indazole derivative at room temperature in the presence of a base such as $NaHCO_3$ or triethylamine in a solvent such as acetonitrile gives the final product vii. Heating vi with a 5-amino-indazole derivative in the absence of base also affords also affords vii.

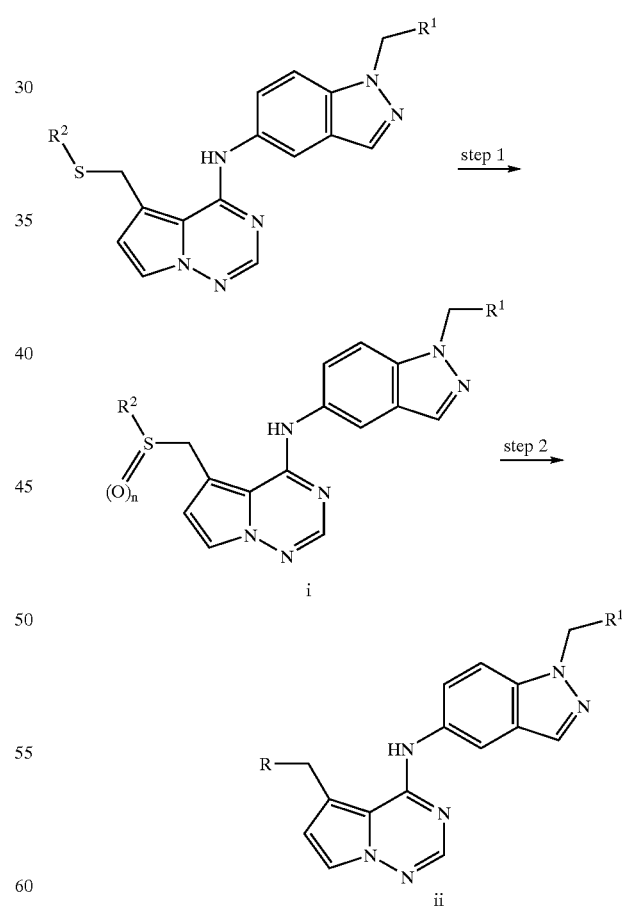

Step 1

Compound vii ($R=SR^2$) of Scheme 1 can be oxidized to the sulfoxide, i (n=1), or the sulfone, i (n=2), of Scheme 2 by treatment with the appropriate amount of an oxidizing agent such as m-chloroperbenzoic acid.

Step 2

The 5-aminomethyl derivative ii is obtained by heating the sulfoxide i (n=1) or the sulfone (n=2) in the presence of an excess of an alcohol or a primary or secondary amine.

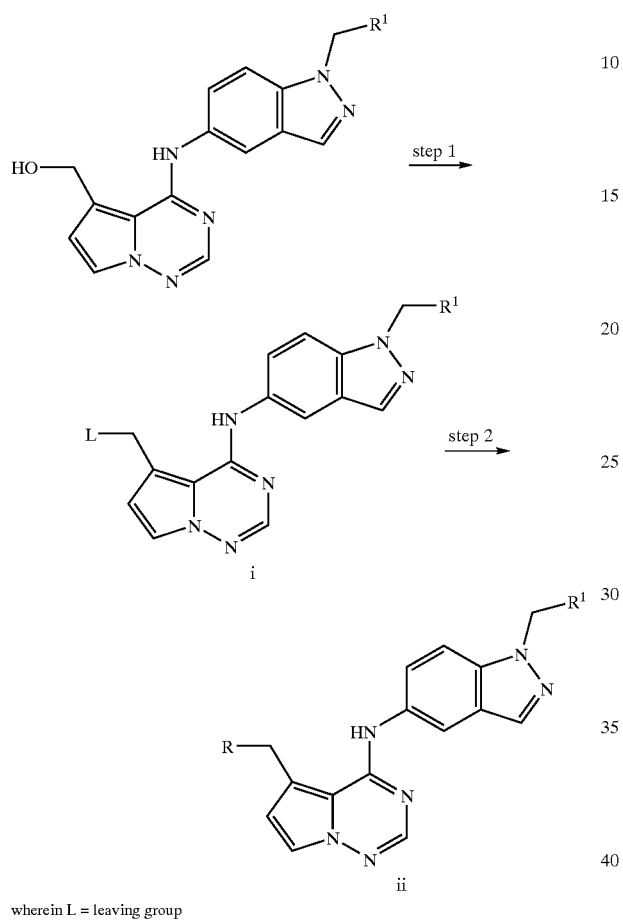

Scheme 3 wherein L = leaving group

Step 1

The alcohol group in compound vii (R=OH) of Scheme 1 can be converted to a leaving group as in compound i of Scheme 3. A variety of leaving groups can be introduced, e.g, treatment with thionyl chloride gives the chloride i (L=Cl), treatment with methanesulfonic anhydride and diisopropylethylamine gives the methanesulfonate i (L=OSO$_2$Me), esterification with acetic anhydride in the presence of diisopropylethylamine gives the acetate i (L=OAc).

Step 2

For very reactive leaving groups such as chloride or sulfonate, i is converted directly into compound ii of Scheme 3 by reaction with an alcohol or a primary or secondary amine in the presence of a base such as diisopropylethylamine without the isolation of i. For less reactive leaving groups such as carboxylates, i is heated with alcohols or a primary or secondary amines in the presence of a base such as diisopropylethylamine to give ii.

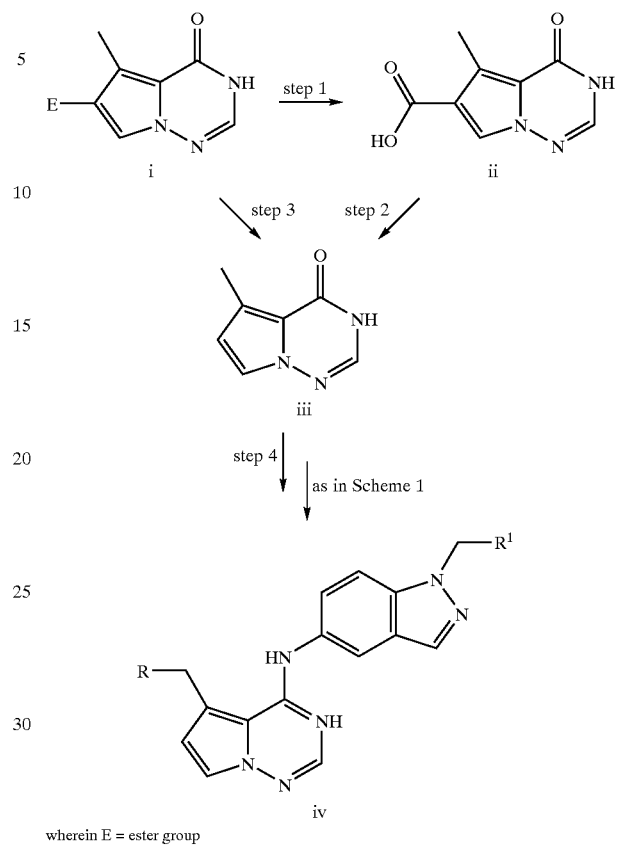

Scheme 4 wherein E = ester group

Step 1

The 5-methyl-4-oxo-3,4-dihydro-pyrrolo[2,1-f][1,2,4] triazine-6-carboxylic acid ester i (see WO 00/71129, herein incorporated by reference) can be saponified by treatment with a base such as an aqueous solution of LiOH and then acidified by treatment with an acid such as HCl to give the carboxylic acid ii of Scheme 4.

Step 2

The carboxylic acid ii is decarboxylated to give the 6H-pyrrolotriazin-4-one iii. This can be accomplished under a variety of conditions, for example, by heating a mixture of ii in 85% H$_3$PO$_4$ at 110° C.

Step 3

The ester i can be converted directly into iii, for example, by heating a mixture of i in 85% H$_3$PO$_4$ at 110° C.

Step 4

The 6H-pyrrolotriazin-4-one iii can be converted into iv as outlined in Scheme 1.

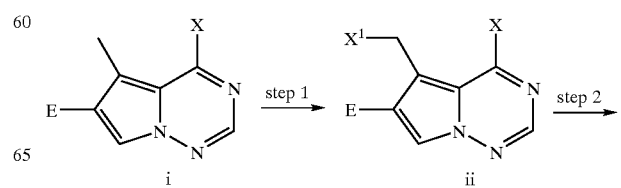

Scheme 5

15

-continued

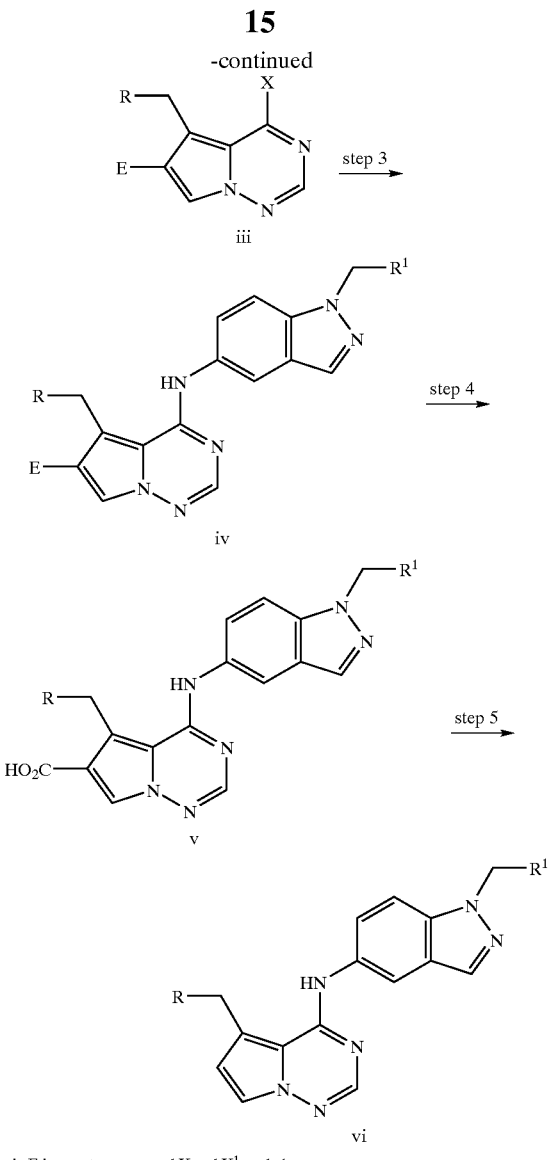

wherein E is an ester group and X and X¹ are halogen

Step 1

Halogenation of the 5-methyl group of 4-halo-5-methyl-pyrrolo[2,1-f][1,2,4]triazine-6-carboxylic acid ester i (see WO 00/71129, herein incorporated by reference) can be effected by treatment of i with a halogenating agent such as a N-bromosuccinimide or sulfuryl chloride. The reaction is performed under an inert atmosphere such as $N_2$ in the presence of a catalyst such dibenzoyl peroxide or 2,2'-azobisisobutyronitrile, or irradiation and gives the 4-halo-5-halomethyl-pyrrolotriazine ii of Scheme 5.

Step 2

Treatment of ii with a thiol, an alcohol, a primary or a secondary amine in the presence of a base such as $NaHCO_3$ or triethylamine in a solvent such as acetonitrile affords intermediate iii.

Step 3

Treatment of iii with a substituted 5-amino-indazole derivative in the presence of a base such as $NaHCO_3$ or triethylamine in a solvent such as acetonitrile gives iv.

Step 4

The ester iv can be saponified by treatment with a base such as an aqueous solution of LiOH and then acidified by treatment with an acid such as HCl to give the carboxylic acid v of Scheme 5.

16

Step 5

The carboxylic acid v of Scheme 5 is decarboxylated by heating to give the final product vi.

In addition, other compounds of formula I may be prepared using procedures generally known to those skilled in the art. In particular, the following examples provide additional methods for the preparation of the compounds of this invention.

The invention will now be further described by the following working examples(s), which are preferred embodiments of the invention. All temperatures are in degrees Celsius (° C.) unless otherwise indicated. "HPLC Ret Time" is the HPLC retention time that was obtained under the following conditions: column type and length, gradient time [unless otherwise indicated, all gradients started with 100% solvent A (10% MeOH, 90% $H_2O$, 0.1% TFA) and ended with 100% solvent B (90% MeOH, 10% $H_2O$, 0.1% TFA)], flow rate (mL/min). UV detection was always conducted at 220 nM. These examples are illustrative rather than limiting and it is to be understood that there may be other embodiments that fall within the spirit and scope of the invention as defined by the claims appended hereto.

EXAMPLE 1

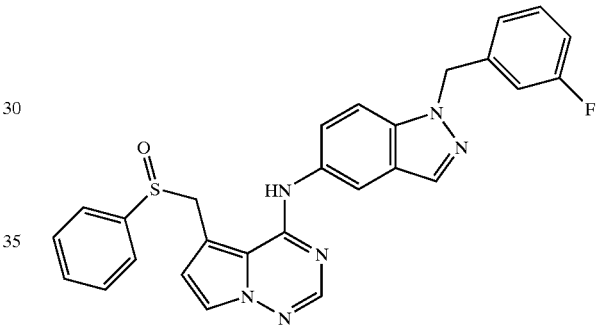

(5-Benzenesulfinylmethyl-pyrrolo[2,1-f][1,2,4]triazin-4-yl)-[1-(3-fluoro-benzyl)-1H-indazol-5-yl]-amine A. Preparation of 5-Methyl-4-oxo-3,4-dihydropyrrolo[2,1-f][1,2,4]triazine-6-carboxylic acid

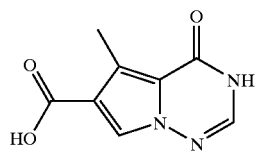

A solution of LiOH (25 gm, 10 equiv) in water (416 mL) was added to a solution of 5-methyl-4-oxo-3,4-dihydro-pyrrolo[2,1-f][1,2,4]triazine-6-carboxylic acid methyl ester (23.0 gm, 0.104 mol) in a mixture of THF (1.2 L) and MeOH (0.4 L). This was heated at 65° C. for 20 h and then concentrated in vacuo to about 200 mL. Water (400 mL) was added and the pH was adjusted to 4 using conc. aqueous HCl. The precipitate was collected, washed with water, and dried to give the acid (18.2 gm, 90%). $^1$H NMR (MeOH-$D_4$) δ 2.67 (s, 3H), 7.63 (s, 1H), 7.84 (s, 1H). HPLC Ret Time: 0.97 min (YMC C18 S5, 4.6×50 mm column, 3 min gradient, 4 mL/min).

B. Preparation of 5-Methyl-3H-pyrrolo[2,1-f][1,2,4]triazin-4-one

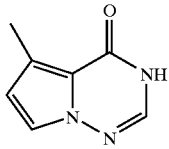

Procedure I: A suspension of 5-methyl-4-oxo-3,4-dihydro-pyrrolo[2,1-f][1,2,4]triazine-6-carboxylic acid (18.1 gm, 93.7 mmole) in 85% aq. $H_3PO_4$ (250 mL) was heated at 110° C. for 3.5 h. After cooling to RT, ice water (500 mL) was added and the precipitate was collected, washed with water, and dried. This afforded 5.8 gm of the product as a brown solid. An additional 4.1 gm (total of 9.9 gm, 71%) of product was obtain by extraction of the filtrate with DCM (4×500 mL), drying ($Na_2SO_4$), and removal of the solvent. $^1$H NMR ($CDCl_3$) δ 2.54 (s, 3H), 6.35 (d, 1H, J=3 Hz), 7.31 (d, 1H, J=3 Hz), 7.42 (s, 1H), 9.52 (br s, 1H); HPLC Ret Time: 1.17 min (YMC C18 S5, 4.6×50 mm column, 3 min gradient, 4 mL/min).

Procedure II: A suspension of 5-methyl-4-oxo-3,4-dihydro-pyrrolo[2,1-f][1,2,4]triazine-6-carboxylic acid methyl ester (5.81 gm, 0.028 mol) in 85% aq. $H_3PO_4$ (60 mL) was heated at 110° C. for 6 h. After cooling to RT, ice (120 gm) was added and the precipitate was collected, washed with water and dried to afforded the product (3.47 gm, 83%).

Procedure III: A solution of 3-methyl-1H-pyrrole-2-carboxylic acid methyl ester (4.59 gm, 33 mmole) in dry DMF (100 mL) was added slowly to an ice cooled suspension of NaH (1.72 gm, 60% dispersion in oil, 1.3 equiv) in dry DMF (300 mL). After 30 min, O-(2,4-dinitro-phenyl)-hydroxylamine (1.53 gm, 1.1 equiv) was added in one portion and the reaction was left stirring in the ice bath for 1 hr. After 0.5 hr it was removed from the bath and diluted with brine. This was extracted with EtOAc (3 times) and the combined extracts were dried ($Na_2SO_4$) and the solvents were removed. The residue was chromatographed on a silica gel column (gradient elution with hexane containing 5 to 20% EtOAc) to give 1-amino-3-methyl-1H-pyrrole-2-carboxylic acid methyl ester (2.96 gm, 58%) as a yellow solid. $^1$H NMR (MeOH-$D_4$) δ 2.25 (s, 3H), 3.81 (s, 3H), 5.83 (d, 1H, J=2 Hz), 6.82 (d, 1H, J=2 Hz); MS: 155 (M+H)$^+$; HPLC Ret Time: 0.97 min (YMC Exterra ODS S7 3.0×50 mm, 2 min gradient, 5 mL/min). A mixture of this 1-amino-pyrrole (2.96 gm, 19.2 mmole) in formamide (30 mL) was heated at 165° C. for 10 hr. After cooling to RT, this was diluted with cold water and the precipitate was collected, washed with cold water followed by a mixture of Et2O and hexane (6:4). This gave 5-methyl-3H-pyrrolo[2,1-f][1,2,4]triazin-4-one (1.83 gm, 64%) as a brown solid.

C. Preparation of 4-Chloro-5-methyl-pyrrolo[2,1-f][1,2,4]triazine

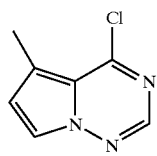

A suspension of of 5-methyl-3H-pyrrolo[2,1-f][1,2,4]triazin-4-one (2.57 gm, 17.2 mmole) in $POCl_3$ (28 mL) was heated at 100° C. for 40 min. The excess reagent was removed under vacuum and the residue was dissolved in DCM (300 mL). This was washed with water, dried ($Na_2SO_4$), and the solvent removed. Flash chromatography on silica gel using DCM as eluent afforded the product as a yellow solid (2.38 gm, 82%). 1HNMR ($CDCl_3$): δ 2.63 (s, 3H), 6.74 (d, 1H, J=2 Hz), 7.74 (d, 1H, J=2 Hz), 8.05 (s, 1H).

D. Preparation of 5-Bromomethyl-4-chloro-pyrrolo[2,1-f][1,2,4]triazine

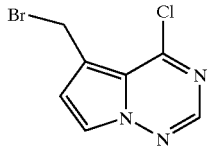

A solution of 4-chloro-5-methyl-pyrrolo[2,1-f][1,2,4]triazine (2.32 gm, 14.0 mmole) in $CCl_4$ (140 mL) was sparged with $N_2$ for 20 min. N-bromosuccinimide (2.60 gm, 1.05 equiv) and benzoyl peroxide (60 mg) were added and the mixture was heated at reflux for 1 hr. After cooling to RT, the succinimide was removed by filtration. The solvent was removed from the filtrate and the residue was quickly chromatographed on a short silica gel column using DCM as the eluent. This afforded the 5-bromomethyl compound as a yellow solid (2.49 gm, 74%). $^1$H NMR ($CDCl_3$): δ 4.96 (s, 2H), 7.03 (d, 1H, J=3 Hz), 7.80 (d, 1H, J=3 Hz), 8.21 (s, 1H).

E. Preparation of 1-(3-Fluoro-benzyl)-1H-indazol-5-ylamine

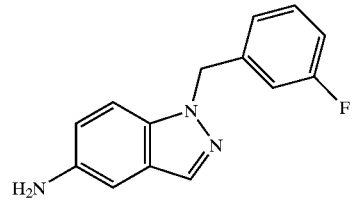

A mixture of 5-nitro-1H-indazole (8.15 gm, 50 mmole), m-fluoro-benzyl chloride (7.95 gm, 1.1 equiv), $K_2CO_3$ (7.59 gm, 1.1 equiv), and KI (8.47 gm, 1.02 equiv) in dry DMF (75 mL) was heated at 70° C. overnight. After cooling to RT, water (75 mL) was slowly added to give a precipitate that consisted of about a one to one mixture of isomers [HPLC Ret Time: 1.92 (1-substitued isomer vs. 2.03 (2-substituted isomer) YMC C18 S5 4.6×50 mm, 3 min gradient, 4 mL/min]. This was collected by filtration and washed with water. The solid was crystallized twice from acetone/water to afford the desired 1-(3-fluoro-benzyl)-5-nitro-1H-indazole (4.47 gm, 33%). A suspension of this material (3.00 gm, 11.1) and 10% Pd/C (3.00 gm) in EtOH (21 mL) was kept under an $H_2$ atmosphere (balloon) for 24 hr. The catalyst was removed by filtration and the solvent was evaporated to leave the product as a solid (2.4 gm, 90%). $^1$H NMR ($CDCl_3$): δ 3.61 (br s, 2H), 5.52 (s, 2H), 6.81–7.85 (m, 7H), 7.85 (s, 1H); MS: 242 (M+H)$^+$; HPLC Ret Time: 1.03 min (YMC Xterra ODS S7, 3.0×50 mm column, 2 min gradient, 5 mL/min).

F. Preparation of (5-Benzenesulfinylmethyl-pyrrolo[2,1-f][1,2,4]triazin-4-yl)-[1-(3-fluoro-benzyl)-1H-indazol-5-yl]-amine A solution of 5-bromomethyl-4-chloro-pyrrolo[2,1-f][1,2,4]triazine (850 mg, 3.46 mmole) in DCM (30 mL) was sparged with $N_2$ for 0.5 hr and then placed in a −20° C. bath.

Thiophenol (384 μL, 1.0 equiv) and diisopropylethylamine (605 μL, 1.0 equiv) were added and the reaction was kept at −20° C. for 3 hr. After warming to RT, the reaction mixture was washed with water, dried (Na$_2$SO$_4$), and the solvent was removed. 1,2-Dichloroethane (10 mL), n-butanol (10 mL) and 1-(3-fluoro-benzyl)-1H-indazol-5-ylamine (750 mg, 0.9 equiv) were added to the residue and this mixture was heated at 85° C. for 2.5 hr. The solvents were removed and the residue was taken up in DCM, washed with sat. aq NaHCO$_3$ solution and dried (Na$_2$SO$_4$). Removal of the solvent followed by chromatography on silica gel using DCM containing 0 to 2% MeOH as eluent afforded [1-(3-fluoro-benzyl)-1H-indazol-5-yl]-(5-phenylsulfanylmethyl-pyrrolo[2,1-f][1,2,4]triazin-4-yl)-amine (957 mg, 58%) as a foam. $^1$H NMR (CDCl$_3$) δ 4.48 (s, 2H), 5.59 (s, 2H), 6.53 (d, 1H, J=3 Hz), 6.8–7.0 (m, 3H), 7.2–7.6 (m, 9H), 7.95 (s, 1H), 8.06 (s, 1H), 8.15 (d, 1H, J=2 Hz), 8.88 (br s, 1H); MS: 481 (M+H)$^+$; HPLC Ret Time: 1.87 min (YMC S7 C18, 3.0×50 mm column, 2 min gradient, 5 mL/min). This was dissolved in chloroform (25 mL), cooled in an ice bath and m-chloroperbenzoic acid (500 mg, 57 to 80%, 1 equiv) was added in small portions over 15 min. After 1 hr., the reaction was washed with 10% aqueous NaHSO$_3$ solution, sat. aq. NaHCO$_3$ solution (three times) and dried (Na$_2$SO$_4$). Removal of the solvent left the product as a foam (957 mg, 95%). $^1$H NMR (CDCl$_3$) δ 4.28 (d, 1H, J=14 Hz), 4.53 (d, 1H, J=14 Hz), 5.60 (s, 2H), 6.13 (d, 1H, J=3 Hz), 6.8–7.6 (m, 11H), 7.71 (dd, 1H, J=2, 9 Hz), 7.98 (s, 1H), 8.05 (s, 1H), 8.14 (d, 1H, J=2 Hz); MS: 497 (M+H)$^+$; HPLC Ret Time: 1.67 min (YMC S7 C18, 3.0×50 mm column, 2 min gradient, 5 mL/min).

EXAMPLE 2

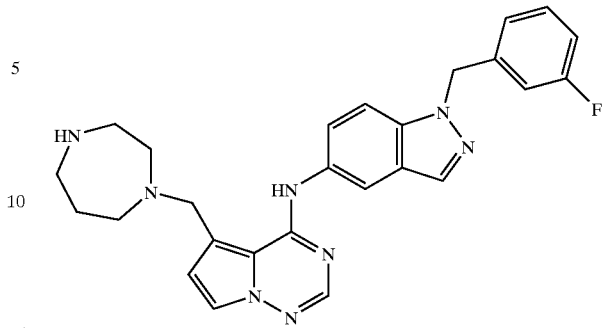

(5-[1,4]Diazepan-1-ylmethyl-pyrrolo[2,1-f][1,2,4]triazin-4-yl)-[1-(3-fluoro-benzyl)-1H-indazol-5-yl]-amine A mixture of (5-benzenesulfinylmethyl-pyrrolo[2,1-f][1,2,4]triazin-4-yl)-[1-(3-fluoro-benzyl)-1H-indazol-5-yl]-amine (50 mg, 0.101 mmole) and homopiperazine (300 mg, 30 equiv) in a sealed tube was heated at 135° C. overnight. The reaction mixture was taken up in DCM, washed with water, and dried (Na$_2$SO$_4$). Removal of the solvent followed by radial chromatography (2 mm silica gel plate eluted with DCM containing 5% MeOH) afforded the title compound as a foam (39 mg, 82%). $^1$H NMR (CDCl$_3$) δ 1.85 (m, 2H), 2.96 (m, 8H), 3.91 (s, 2H), 5.58 (s, 2H), 6.50 (d, 1H, J=3 Hz), 6.8–7.6 (m, 7H), 7.89 (s, 1H), 8.05 (d, 1H, J=1 Hz), 8.11 (d, 1H, J=2 Hz); MS: 471 (M+H)$^+$; HPLC Ret Time: 1.09 min (YMC Xterra ODS S7, 3.0×50 mm column, 2 min gradient, 5 mL/min).

EXAMPLES 3 to 73

The follow examples were prepared in the same manner as Example 2.

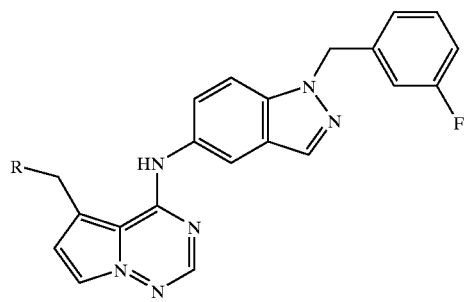

| Ex. | R | Compound Name | HPLC Ret Time (min) |
|---|---|---|---|
| 3 | ![imidazole] | [1-(3-Fluoro-benzyl)-1H-indazol-5-yl]-(5-imidazol-1-ylmethyl-pyrrolo[2,1-f][1,2,4]triazin-4-yl)-amine | 1.21 |
| 4 | ![imidazolylpropylamine] | [1-(3-Fluoro-benzyl)-1H-indazol-5-yl]-{5-[(3-imidazol-1-yl-propylamino)-methyl]-pyrrolo[2,1-f][1,2,4]triazin-4-yl}-amine | 1.12 |
| 5 | NC~NMe | [1-(3-Fluoro-benzyl)-1H-indazol-5-yl]-(5-{[(2-cyano-ethyl)-methyl-amino]-methyl}-pyrrolo[2,1-f][1,2,4]triazin-4-yl)-amine | 1.29 |

-continued

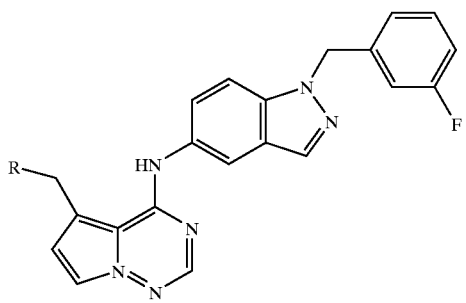

| Ex. | R | Compound Name | HPLC Ret Time (min) |
|---|---|---|---|
| 6 | 2-pyridin-2-yl-piperazin-1-yl | [1-(3-Fluoro-benzyl)-1H-indazol-5-yl]-[5-(4-pyridin-2-yl-piperazin-1-ylmethyl)-pyrrolo[2,1-f][1,2,4]triazin-4-yl]-amine | 1.17 |
| 7 | Me₂N-CH₂CH₂-NMe | N-{4-[1-(3-Fluoro-benzyl)-1H-indazol-5-ylamino]-pyrrolo[2,1-f][1,2,4]triazin-5-ylmethyl}-N,N',N'-trimethyl-ethane-1,2-diamine | 1.17 |
| 8 | AcNH-CH₂CH₂-(imidazol-4-yl) | N-[2-(1-{4-[1-(3-Fluoro-benzyl)-1H-indazol-5-ylamino]pyrrolo[2,1-f][1,2,4]triazin-5-ylmethyl}-1H-imidazol-4-yl)-ethyl]acetamide | 1.22 |
| 9 | HO-CH₂CH₂-NMe | 2-({4-[1-(3-Fluoro-benzyl)-1H-indazol-5-ylamino]pyrrolo[2,1-f][1,2,4]triazin-5-ylmethyl}-methyl-amino)-ethanol | 1.20 |
| 10 | (MeO)₂CH-CH₂-NMe | (5-{[(2,2-Dimethoxy-ethyl)-methyl-amino]methyl}-pyrrolo[2,1-f][1,2,4]triazin-4-yl)-[1-(3-fluoro-benzyl)-1H-indazol-5-yl]-amine | 1.32 |
| 11 | piperidine-3-carboxamide | 1-{4-[1-(3-Fluoro-benzyl)-1H-indazol-5-ylamino]pyrrolo[2,1-f][1,2,4]triazin-5-ylmethyl}-piperidine-3-carboxylic acid amide | 1.23 |
| 12 | pyridin-4-ylmethyl-NEt | 5-[(Ethyl-pyridin-4-ylmethyl-amino)-methyl]pyrrolo[2,1-f][1,2,4]triazin-4-yl}-[1-(3-fluoro-benzyl)-1H-indazol-5-yl]-amine | 1.29 |
| 13 | [1,3]dioxolan-2-ylmethyl-NMe | {5-[([1,3]Dioxolan-2-ylmethyl-methyl-amino)-methyl]-pyrrolo[2,1-f][1,2,4]triazin-4-yl}-[1-(3-fluoro-benzyl)-1H-indazol-5-yl]amine | 1.30 |
| 14 | 4-methyl-piperazin-1-yl | [1-(3-Fluoro-benzyl)-1H-indazol-5-yl]-[5-(4-methyl-piperazin-1-ylmethyl)-pyrrolo[2,1-f][1,2,4]triazin-4-yl]-amine | 1.14 |
| 15 | 4-pyrazin-2-yl-piperazin-1-yl | [1-(3-Fluoro-benzyl)-1H-indazol-5-yl][5-(2,3,5,6-tetrahydro-[1,2']bipyrazinyl-4-ylmethyl)-pyrrolo[2,1-f][1,2,4]triazin-4-yl]amine | 1.35 |
| 16 | HO-CH₂CH₂-piperazin-1-yl | 2-(4-{4-[1-(3-Fluoro-benzyl)-1H-indazol-5-ylamino]pyrrolo[2,1-f][1,2,4]triazin-5-ylmethyl}-piperazin-1-yl)-ethanol | 1.12 |

-continued

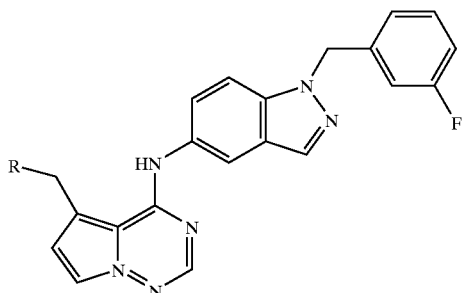

| Ex. | R | Compound Name | HPLC Ret Time (min) |
|---|---|---|---|
| 17 | (morpholine-ethyl-piperazine) | 2-(4-{4-[1-(3-Fluoro-benzyl)-1H-indazol-5-ylamino]pyrrolo[2,1-f][1,2,4]triazin-5-ylmethyl}-piperazin-1-yl)-ethanol | 1.12 |
| 18 | (acetyl-piperazine) | 1-(4-{4-[1-(3-Fluoro-benzyl)-1H-indazol-5-ylamino]pyrrolo[2,1-f][1,2,4]triazin-5-ylmethyl}-piperazin-1-yl)-ethanone | 1.22 |
| 19 | (N-methyl-piperidine-NMe) | [1-(3-Fluoro-benzyl)-1H-indazol-5-yl]-(5-{[methyl-(1-methyl-piperidin-4-yl)-amino]methyl}-pyrrolo[2,1-f][1,2,4]triazin-4-yl)-amine | 0.97* |
| 20 | Me2N-propyl-NMe | N-{4-[1-(3-Fluoro-benzyl)-1H-indazol-5-ylamino]-pyrrolo[2,1-f][1,2,4]triazin-5-ylmethyl}-N,N',N'-trimethyl-propane-1,3-diamine | 0.95* |
| 21 | (morpholino-ethyl-NH) | [1-(3-Fluoro-benzyl)-1H-indazol-5-yl]-{5-[(2-morpholin-4-yl-ethylamino)-methyl]-pyrrolo[2,1-f][1,2,4]triazin-4-yl}-amine | 1.13 |
| 22 | (morpholino-propyl-NH) | [1-(3-Fluoro-benzyl)-1H-indazol-5-yl]-{5-[(3-morpholin-4-yl-propylamino)-methyl]-pyrrolo[2,1-f][1,2,4]triazin-4-yl}-amine | 1.11 |
| 23 | Me2N-C(O)-CH2-NMe | 2-({4-[1-(3-Fluoro-benzyl)-1H-indazol-5-ylamino]-pyrrolo[2,1-f][1,2,4]triazin-5-ylmethyl}-methyl-amino)-N,N-dimethyl-acetamide | 1.19 |
| 24 | (2,5-dihydropyrrole) | [5-(2,5-Dihydro-pyrrol-1-ylmethyl)-pyrrolo[2,1-f][1,2,4]triazin-4-yl]-[1-(3-fluoro-benzyl)-1H-indazol-5-yl]-amine | 1.32 |
| 25 | (furfuryl-NMe) | [1-(3-Fluoro-benzyl)-1H-indazol-5-yl]-{5-[(furan-2-ylmethyl-methyl-amino)-methyl]-pyrrolo[2,1-f][1,2,4]triazin-4-yl}-amine | 1.46 |
| 26 | MeO-ethyl-piperazine | [1-(3-Fluoro-benzyl)-1H-indazol-5-yl]-{5-[4-(2-methoxy-ethyl)-piperazin-1-ylmethyl]-pyrrolo[2,1f][1,2,4]triazin-4-yl}-amine | 1.23 |
| 27 | (pyrrolidine) | [1-(3-Fluoro-benzyl)-1H-indazol-5-yl]-(5-pyrrolidin-1-ylmethyl-pyrrolo[2,1-f][1,2,4]triazin-4-yl)-amine | 1.31 |

-continued

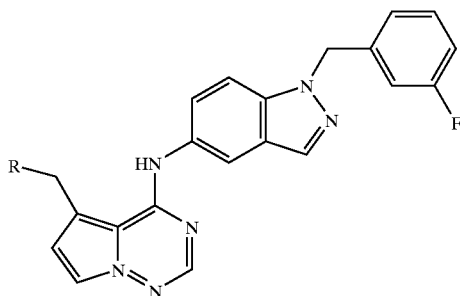

| Ex. | R | Compound Name | HPLC Ret Time (min) |
|---|---|---|---|
| 28 | Me₂N-pyrrolidine (racemic) | [5-(3-Dimethylamino-pyrrolidin-1-ylmethyl)-pyrrolo[2,1-f][1,2,4]triazin-4-yl]-[1-(3-fluoro-benzyl)-1H-indazol-5-yl]-amine | 1.21 |
| 29 | MeO-CH₂CH₂-NMe | [1-(3-Fluoro-benzyl)-1H-indazol-5-yl]-(5-{[(2-methoxy-ethyl)-methyl-amino]-methyl}-pyrrolo{2,1-f][1,2,4]triazin-4-yl)-amine | 1.20* |
| 30 | HO-pyrrolidine | 1-{4-[1-(3-Fluoro-benzyl)-1H-indazol-5-ylamino]-pyrrolo[2,1-f][1,2,4]triazin-5-ylmethyl}-(3R)-pyrrolidin-3-ol | 1.10* |
| 31 | MeHN-CH₂CH₂-NMe | N-{4-[1-(3-Fluoro-benzyl)-1H-indazol-5-ylamino]-pyrrolo[2,1-f][1,2,4]triazin-5-ylmethyl}-N,N'-dimethyl-ethane-1,2-diamine | 0.98* |
| 32 | pyrrolidine-CONH₂ | 1-{4-[1-(3-Fluoro-benzyl)-1H-indazol-5-ylamino]-pyrrolo[2,1-f][1,2,4]triazin-5-ylmethyl}-(2S)-pyrrolidine-2-carboxylic acid amide | 1.11* |
| 33 | pyrrolidine-CH₂OH | (1-{4-[1-(3-Fluoro-benzyl)-1H-indazol-5-ylamino]-pyrrolo[2,1-f][1,2,4]triazin-5-ylmethyl}-(2S)-pyrrolidin-2-yl)-methanol | 1.11* |
| 34 | HO-CH₂-piperidine | (1-{4-[1-(3-Fluoro-benzyl)-1H-indazol-5-ylamino]-pyrrolo[2,1-f][1,2,4]triazin-5-ylmethyl}-piperidin-4-yl)-methanol | 1.26 |
| 35 | OH-CH₂-piperidine (racemic) | (1-{4-[1-(3-Fluoro-benzyl)-1H-indazol-5-ylamino]-pyrrolo[2,1-f][1,2,4]triazin-5-ylmethyl}-piperidin-3-yl)-methanol | 1.28 |
| 36 | HO-piperidine | 1-{4-[1-(3-Fluoro-benzyl)-1H-indazol-5-ylamino]-pyrrolo[2,1-f][1,2,4]triazin-5-ylmethyl}-piperidin-4-ol | 1.10* |

-continued

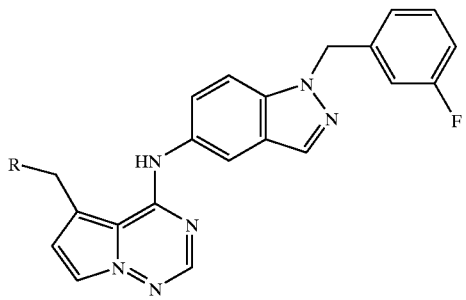

| Ex. | R | Compound Name | HPLC Ret Time (min) |
|---|---|---|---|
| 37 |  | 1-{4-[1-(3-Fluoro-benzyl)-1H-indazol-5-ylamino]-pyrrolo[2,1-f][1,2,4]triazin-5-ylmethyl}-piperidine-4-carboxylic acid amide | 1.24 |
| 38 |  | (1-{4-[1-(3-Fluoro-benzyl)-1H-indazol-5-ylamino]-pyrrolo[2,1-f][1,2,4]triazin-5-ylmethyl}-(2R)-pyrrolidin-2-yl)-methanol | 1.11* |
| 39 |  | [1-({4-[1-(3-Fluoro-benzyl)-1H-indazol-5-ylamino]-pyrrolo[2,1-f][1,2,4]triazin-5-ylmethyl}-amino)-cyclopentyl]-methanol | 1.43 |
| 40 |  | (2R)-3-({4-[1-(3-Fluoro-benzyl)-1H-indazol-5-ylamino]-pyrrolo[2,1-f][1,2,4]triazin-5-ylmethyl}-amino)-propane-1,2-diol | 1.25 |
| 41 |  | Trans-4-({4-[1-(3-fluoro-benzyl)-1H-indazol-5-ylamino]-pyrrolo[2,1-f][1,2,4]triazin-5-ylmethyl}-amino)-cyclohexanol | 1.30 |
| 42 |  | (5-Cyclopentylaminomethyl-pyrrolo[2,1-f][1,2,4]triazin-4-yl)-[1-(3-fluoro-benzyl)-1H-indazol-5-yl]-amine | 1.46 |
| 43 |  | 2-({4-[1-(3-Fluoro-benzyl)-1H-indazol-5-ylamino]-pyrrolo[2,1-f][1,2,4]triazin-5-ylmethyl}-amino)-ethanol | 1.24 |
| 44 |  | 1-{4-[1-(3-Fluoro-benzyl)-1H-indazol-5-ylamino]-pyrrolo[2,1-f][1,2,4]triazin-5-ylmethyl}-(3S)-pyrrolidin-3-ol | 1.27 |
| 45 |  | [5-(1,4-Dioxa-8-aza-spiro[4.5]dec-8-ylmethyl)-pyrrolo[2,1-f][1,2,4]triazin-4-yl]-[1-(3-fluoro-benzyl)-1H-indazol-5-yl]-amine | 1.35 |

-continued

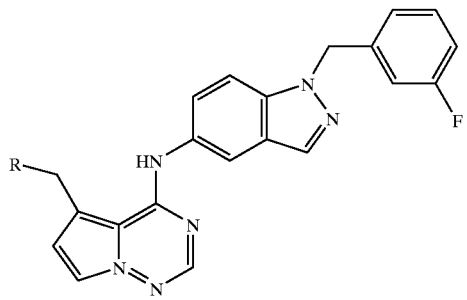

| Ex. | R | Compound Name | HPLC Ret Time (min) |
|---|---|---|---|
| 46 | NC-CH2CH2-piperazinyl | [1-(3-Fluoro-benzyl)-1H-indazol-5-yl]-{5-[4-(2-cyano-ethyl)-piperazin-1-ylmethyl]-pyrrolo[2,1-f][1,2,4]triazin-4-yl}-amine | 1.01* |
| 47 | NC-CH2-cyclohexyl-CH2-piperazinyl | [1-(3-Fluoro-benzyl)-1H-indazol-5-yl]-[5-(4-cyanomethyl-cyclohexylmethyl)-pyrrolo[2,1-f][1,2,4]triazin-4-yl]-amine | 1.30 |
| 48 | methanesulfonyl-ethyl-piperazinyl | [1-(3-Fluoro-benzyl)-1H-indazol-5-yl]-{5-[4-(2-methanesulfonyl-ethyl)-piperazin-1-ylmethyl]-pyrrolo[2,1-f][1,2,4]triazin-4-yl}-amine | 1.22 |
| 49 | H2N-C(O)-CH2CH2-NH- | 3-({4-[1-(3-Fluoro-benzyl)-1H-indazol-5-ylamino]-pyrrolo[2,1-f][1,2,4]triazin-5-ylmethyl}-amino)-propionamide | 1.26 |
| 50 | 3,5-dimethylpiperazinyl (diastereomeric mixture) | [5-(3,5-Dimethyl-piperazin-1-ylmethyl)-pyrrolo[2,1-f][1,2,4]triazin-4-yl]-[1-(3-fluoro-benzyl)-1H-indazol-5-yl]-amine | 1.06* |
| 51 | 2,5-diaza-bicyclo[2.2.1]heptyl | [5-(2,5-Diaza-bicyclo[2.2.1]hept-2-ylmethyl)-pyrrolo[2,1-f][1,2,4]triazin-4-yl]-[1-(3-fluoro-benzyl)-1H-indazol-5-yl]-amine | 1.17 |
| 52 | HO-C(CH3)2-CH2-NH- | 2-({4-[1-(3-Fluoro-benzyl)-1H-indazol-5-ylamino]-pyrrolo[2,1-f][1,2,4]triazin-5-ylmethyl}-amino)-propan-2-ol | 1.35 |
| 53 | (3S)-3-methylpiperazinyl | [1-(3-Fluoro-benzyl)-1H-indazol-5-yl]-[5-((3S)-3-methyl-piperazin-1-ylmethyl)-pyrrolo[2,1-f][1,2,4]triazin-4-yl]-amine | 1.02* |

-continued

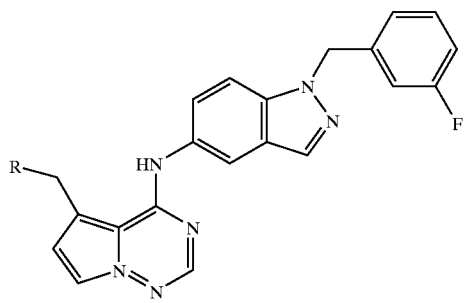

| Ex. | R | Compound Name | HPLC Ret Time (min) |
|---|---|---|---|
| 54 | (trans-2,5-dimethyl-piperazinyl-methyl, HN) | [5-(Trans-2,5-dimethyl-piperazin-1-ylmethyl)-pyrrolo[2,1-f][1,2,4]triazin-4-yl]-[1-(3-fluoro-benzyl)-1H-indazol-5-yl]-amine | 1.27 |
| 55 | piperazine-2-carboxamide (racemic) | 1-{4-[1-(3-Fluoro-benzyl)-1H-indazol-5-ylamino]-pyrrolo[2,1-f][1,2,4]triazin-5-ylmethyl}-piperazine-2-carboxylic acid amide | 1.07 |
| 56 | piperazine-2-carboxamide (racemic) | 4-{4-[1-(3-Fluoro-benzyl)-1H-indazoL-5-ylamino]-pyrrolo[2,1-f][1,2,4]triazin-5-ylmethyl}-piperazine-2-carboxylic acid amide | 1.17 |
| 57 | piperazin-2-one | 4-{4-[1-(3-Fluoro-benzyl)-1H-indazol-5-ylamino]-pyrrolo[2,1-f][1,2,4]triazin-5-ylmethyl}-piperazin-2-one | 1.24 |
| 58 | (3R)-3-hydroxypiperidine | 1-{4-[1-(3-Fluoro-benzyl)-1H-indazol-5-ylamino]-pyrrolo[2,1-f][1,2,4]triazin-5-ylmethyl}-(3R)-piperidin-3-ol | 1.29 |
| 59 | (2S)-2-amino-propan-1-ol | (2S)-2-({4-[1-(3-Fluoro-benzyl)-1H-indazol-5-ylamino]-pyrrolo[2,1-f][1,2,4]triazin-5-ylmethyl}-amino)-propan-1-ol | 1.26 |
| 60 | (2R)-2-amino-propan-1-ol | (2R)-2-({4-[1-(3-Fluoro-benzyl)-1H-indazol-5-ylamino]-pyrrolo[2,1-f][1,2,4]triazin-5-ylmethyl}-amino)-propan-1-ol | 1.26 |
| 61 | 2-amino-2-methyl-propane-1,3-diol | 2-({4-[1-(3-Fluoro-benzyl)-1H-indazol-5-ylamino]-pyrrolo[2,1-f][1,2,4]triazin-5-ylmethyl}-amino)-2-methyl-propane-1,3-diol | 1.25 |

-continued

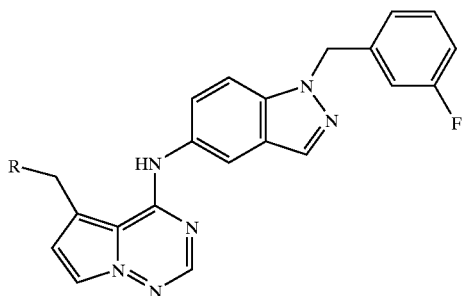

| Ex. | R | Compound Name | HPLC Ret Time (min) |
|---|---|---|---|
| 62 | HO, HO with NH | 2-({4-[1-(3-Fluoro-benzyl)-1H-indazol-5-ylamino]-pyrrolo[2,1-f][1,2,4]triazin-5-ylmethyl}-amino)-propane-1,3-diol | 1.21 |
| 63 | HN-piperazine | [1-(3-Fluoro-benzyl)-1H-indazol]-5-yl]-(5-piperazin-1-ylmethyl-pyrrolo[2,1-f][1,2,4]triazin-4-yl)amine | 1.02 |
| 64 | S-thiomorpholine | [1-(3-Fluoro-benzyl)-1H-indazol-5-yl]-[5-(thiomorpholin-4-ylmethyl)-pyrrolo[2,1-f][1,2,4]triazin-4-yl]-amine | 1.92 |
| 65 | H$_2$N-cyclohexyl-N | N-{4-[1-(3-Fluoro-benzyl)-1H-indazol-5-ylamino]-pyrrolo[2,1-f][1,2,4]triazin-5-ylmethyl}-transcyclohexane-1,4-diamine | 1.09** |
| 66 | H$_2$N, Me-piperidine | [5-(4-Amino-4-methyl-piperidin-1-ylmethyl)-pyrrolo[2,1-f][1,2,4]triazin-4-yl]-[1-(3-fluoro-benzyl)-1H-indazol-5-yl]-amine | 0.99** |
| 67 | NC-piperidine | 1-{4-[1-(3-Fluoro-benzyl)-1H-indazol-5-ylamino]-pyrrolo[2,1-f][1,2,4]triazin-5-ylmethyl}-piperidine-4-carbonitrile | 1.28 |
| 68 | MeO-CH$_2$CH$_2$-NH-piperidine | [1-(3-Fluoro-benzyl)-1H-indazol-5-yl]-{5-[4-(2-methoxy-ethylamino)-piperidin-1-ylmethyl]-pyrrolo[2,1-f][1,2,4]triazin-4-yl}-amine | 1.30 |
| 69 | diazepan-5-one | 1-{4-[1-(3-Fluoro-benzyl)-1H-indazol-5-ylamino]-pyrrolo[2,1-f][1,2,4]triazin-5-ylmethyl}-[1,4]diazepan-5-one | 2.05*** |
| 70 | MeO$_2$C-piperidine | 1-{4-[1-(3-Fluoro-benzyl)-1H-indazol-5-ylamino]-pyrrolo[2,1-f][1,2,4]triazin-5-ylmethyl}-piperidine-4-carboxylic acid methyl ester | 1.41 |
| 71 | H$_2$N-piperidine | [5-(4-Amino-piperidin-1-ylmethyl)-pyrrolo[2,1-f][1,2,4]triazin-4-yl]-[1-(3-fluoro-benzyl)-1H-indazol-5-yl]-amine | 1.03* |

-continued

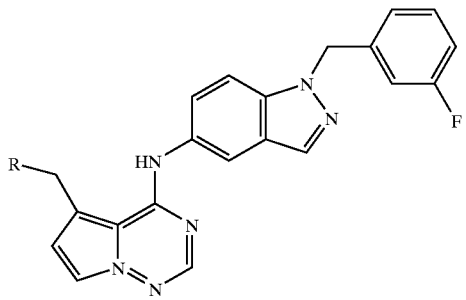

| Ex. | R | Compound Name | HPLC Ret Time (min) |
|---|---|---|---|
| 72 | (H₂N, methyl-piperidinyl) | (±)-[5-(cis-4-Amino-3-methyl-piperidin-1-ylmethyl)-pyrrolo[2,1-f][1,2,4]triazin-4-yl]-[1-(3-fluoro-benzyl)-1H-indazol-5-yl]-amine | 1.08* |
| 73 | (H₂N, methyl-piperidinyl) | (±)-[5-(trans-4-Amino-3-methyl-piperidin-1-ylmethyl)-pyrrolo[2,1-f][1,2,4]triazin-4-yl]-[1-(3-fluoro-benzyl)-1H-indazol-5-yl]-amine | 1.31 |

Unless otherwise indicated, HPLC Retention Times were determined using a YMC Xterra ODS S7 3.0 × 50 mm column with a 2 minute gradient time and a flow rate of 5 mL/min. HPLC Retention Times marked with a "*" were determined using a YMC S7 C18 3.0 × 50 mm column with a 2 minute gradient time and a flow rate of 5 mL/min, with "" were determined using a YMC ODS-A S7 C18 3.0 × 50 mm column with a 2 minute gradient time and a flow rate of 5 mL/min, and those with "*" were determined using a YMC ODS-A C18 S5 4.6 × 33 mm column with a 4 minute gradient time and a flow rate of 4 mL/min

EXAMPLE 74

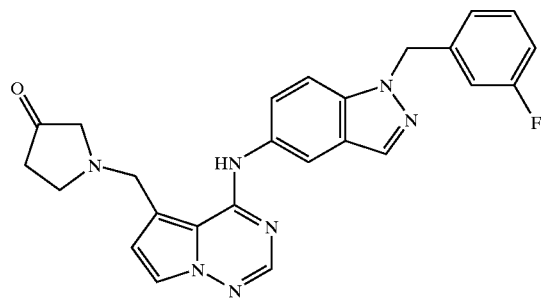

1-{4-[1-(3-Fluoro-benzyl)-1H-indazol-5-ylamino]-pyrrolo[2,1-f][1,2,4]triazin-5-ylmethyl}-pyrrolidin-3-one Tetrapropylammonium perruthenate (3.2 mg, 0.1 equiv) was added to a stirred suspension of 1-{4-[1-(3-fluoro-benzyl)-1H-indazol-5-ylamino]-pyrrolo[2,1f][1,2,4]triazin-5-ylmethyl}-(3R)-pyrrolidin-3-ol (42 mg, 0.092 mmole), N-methylmorpholine N-oxide (16 mg, 1.5 equiv), and dried, powdered 4A molecular sieves (100 mg) in dry DCM under N₂. After 0.75 hr, the dark green suspension was filtered through a short pad of silica gel using ethyl acetate as eluent. Removal of the solvent from the fractions containing the product followed by radial chromatography (2 mm silica gel plate employing gradient elution with mixtures of hexane containing 30 to 50% EtOAc) afforded the title compound as an oil (26 mg, 61%). MS: 456 (M+H)⁺; HPLC Ret Time: 1.28 min (YMC Xterra ODS S7 C18, 3.0×50 mm column, 2 min gradient, 5 mL/min).

EXAMPLE 75

1-{4-[1-(3-Fluoro-benzyl)-1H-indazol-5-ylamino]-pyrrolo[2,1-f][1,2,4]triazin-5-ylmethyl}-piperidin-4-one A solution of [5-(1,4-dioxa-8-aza-spiro[4.5]dec-8-ylmethyl)-pyrrolo[2,1-f][1,2,4]triazin-4-yl]-[1-(3-fluoro-benzyl)-1H-indazol-5-yl]-amine (54 mg, 0.105 mmole) in a mixture of THF (1 mL) and 1 N aq. HCl (1 mL) containing 16 drops of conc. HCl was left stirring a RT for 7 days. The reaction was diluted with DCM and neutralized with sat. aq. NaHCO₃ solution. After drying (Na₂SO₄), the solvent was removed to leave the title compound as an oil (19 mg, 39%). MS: 488 (M+H₂O+H)⁺; HPLC Ret Time: 2.35 min (YMC Xterra ODS S7 C18, 3.0×50 mm column, 5 min gradient (component B was varied from 20 to 60%), 5 mL/min).

EXAMPLE 76

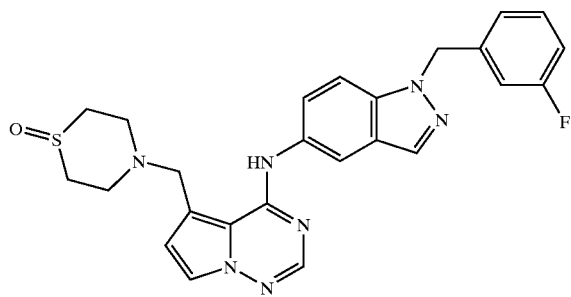

[1-(3-Fluoro-benzyl)-1H-indazol-5-yl]-[5-(1-oxo-1λ⁴-thiomorpholin-4-ylmethyl)-pyrrolo[2,1-f][1,2,4]triazin-4-yl]-amine A solution of [1-(3-fluoro-benzyl)-1H-indazol-5-yl]-[5-(thiomorpholin-4-ylmethyl)-pyrrolo[2,1-f][1,2,4]triazin-4-yl]-amine (46 mg, 0.096 mmole) in chloroform (2 mL) was cooled in an ice bath and m-chloroperbenzoic acid (26 mg, 65%, 1 equiv) was added in portions over 12 min. After 1 hr, the reaction was then diluted with chloroform, washed with 6% aq. NaHSO₃ solution, sat. aq. NaHCO₃ solution and dried (Na₂SO₄). The solvent was removed and purification by radial chromatography (2 mm silica gel plate employing gradient elution with DCM containing 0 to 5% MeOH) afforded the title compound as an oil (13 mg, 27%). MS: 490 (M+H)⁺; HPLC Ret Time: 1.62 min (YMC S5 C18, 4.60×50 mm column, 3 min gradient, 4 mL/min).

EXAMPLE 77

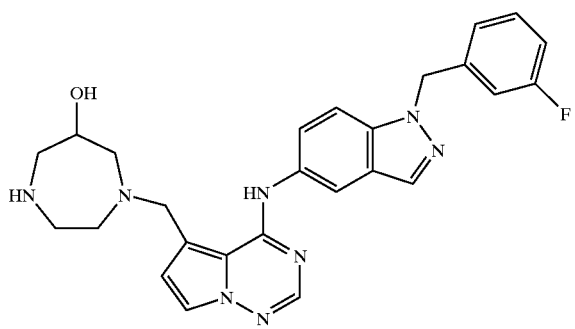

(1-{4-[1-(3-Fluoro-benzyl)-1H-indazol-5-ylamino]-pyrrolo[2,1-f][1,2,4]triazin-5-ylmethyl}-(±)-[1,4]diazepan-6-ol A mixture of (5-benzenesulfinylmethyl-pyrrolo[2,1-f][1,2,4]triazin-4-yl)-[1-(3-fluoro-benzyl)-1H-indazol-5-yl]-amine (397 mg, 0.8 mmole) and [1,4]diazepan-6-ol (417 mg, 4.5 equiv, Saari et al., J. Org. Chem., 1971, 36, 1711) in dry DMSO (1.5 mL) in a sealed tube was heated at 140° C. for 11 hr. This was diluted with DCM (150 ml), washed with water and dried (Na₂SO₄). Removal of the solvent followed by radial chromatography (4 mm silica gel plate; gradient elution with DCM containing 0 to 3% of a 2N NH₃ solution in MeOH) gave the title compound as a solid (242 mg, 62%), MS: 487 (M+H)⁺; HPLC Ret Time: 0.96 min (Xterra S7 3.0×50 mm S7 C18 column, 2 min gradient, 5 ml/min).

The racemic material could be separated on a Chiralpak AD 4.6×250 mm column, eluting with 0.05% diethylamine in EtOH for 25 min with a flow rate of 0.7 mL/min) The S and R enantiomers had retention times of 16.20 and 18.90 min respectively. The R enantiomer was synthesized as outlined below.

EXAMPLES 78

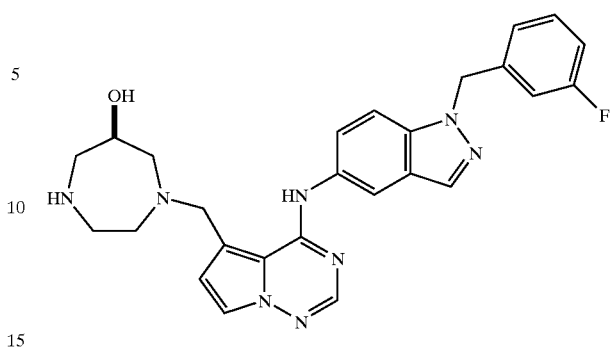

1-{4-[1-(3-Fluoro-benzyl)-1H-indazol-5-ylamino]-pyrrolo[2,1-f][1,2,4]triazin-5-ylmethyl}-(6R)-[1,4]diazepan-6-ol

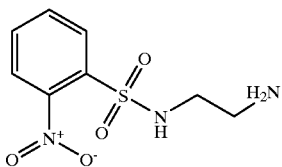

A. Preparation of N-(2-Amino-ethyl)-2-nitro-benzenesulfonamide

A solution of ethylene diamine (268 mL, 20 equiv) in DCM (400 mL) was added to an ice-cooled solution of o-nitrobenzene sulfonyl chloride (44.4 gm, 0.2 mole) in DCM (200 mL) over 1 hr. Concentration on the rotary evaporator left an oil which was partitioned between DCM and sat. aq. Na₂CO₃ solution. The aqueous phase was backextracted with DCM and the combined organic phases were dried (Na₂SO₄). Removal of the solvents followed by silica gel chromatography (step gradient elution with DCM containing 0, 5, 10, 20, 30% MeOH) afforded the title compound as an oil (37.2 gm, 76%). ¹H NMR (CDCl₃+D₂O) δ 2.82 (t, 2H, J=5.1 Hz), 3.10 (t, 2H, J=5.1 Hz), 7.73 (m, 2H), 7.83 (m, 1H), 8.11 (m, 1H); MS: 246 (M+H)⁺; HPLC Ret Time: 0.39 min (YMC Xterra 3.0×50 mm S7 C18 column, 3 min gradient, 4 mL/min).

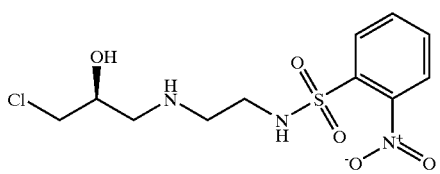

B. Preparation of N-[2-({2S}-3-Chloro-2-hydroxy-propylamino)-ethyl]-2-nitro-benzenesulfonamide S-(+)-epichlorohydrin (5.92 mL, 0.5 equiv) was added to a suspension of N-(2-amino-ethyl)-2-nitro-benzenesulfonamide (37.2 gm, 0.152 mole) and MgSO₄ (9.1 gm, 0.5 equiv) in dry MeOH (38 mL) at RT. After 8 hr, the solid was removed by filtration. The filtrate was concentrated and partitioned between DCM and water. The organic phase was separated, dried (Na₂SO₄) and the solvent was removed. Silica gel chromatorgraphy (step gradient elution with DCM containing 0, 1, 1.5, 2, 2.5, 3% MeOH) afforded the title compound as an oil (20.73 gm, 81%). ¹H NMR (CDCl₃+D₂O) δ 2.59–2.76 (m, 2H), 2,80 (t, 2H, J=5.4 Hz), 3.17 (t, 2H, J=5.4 Hz), 3.53 (d, 2H, J=5.7 Hz), 3.79 (m, 1H), 7.74 (m, 2H), 7.85 (m, 1H), 8.13 (m, 1H); MS: 338 (M+H⁺); HPLC Ret Time: 0.67 min (YMC Xterra 3.0×50 mm S7 C18 column, 3 min gradient, 4 mL/min).

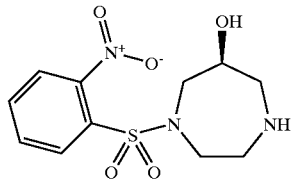

C. Preparation of 1-(2-Nitro-benzenesulfonyl)-(6S)-[1,4]diazepan-6-ol

A suspension of N-[2-({2S}-3-chloro-2-hydroxy-propylamino)-ethyl]-2-nitro-benzenesulfonamide (20.73 gm, 61.4 mmole) and Cs₂CO₃ (73 gm, 3 equiv) in dry acetonitrile (600 mL) under a N₂ atmosphere was heated at 60° C. for 6.5 hr. The solid was removed by filtration and then the solvent was removed from the filtrate. The residue was partitioned between DCM (400 mL) and water (100 mL). The organic phase was dried (Na₂SO₄) and the solvent was removed. Silica gel chromatography (step gradient elution with DCM containing: 0, 1, 2, 3, 4% MeOH) afforded the title compound as an oil (5.68 gm, 31%). ¹H NMR (CDCl₃+D₂O) δ 2.3 (br. s, 2H), 2,85 (m, 4H), 3.09 (m, 4H), 7.68 (m, 3H), 8.00 (m, 1H); MS: 302 (M+H⁺); HPLC Ret Time: 0.56 min (YMC Xterra 3.0×50 mm S7 C18 column, 3 min gradient, 4 mL/min).

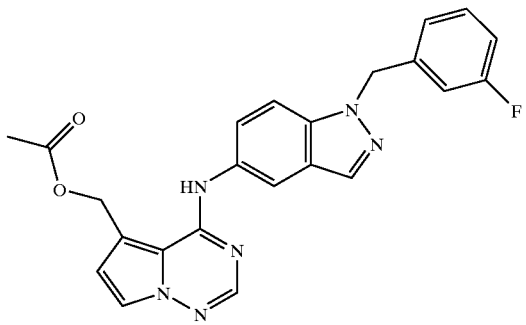

D. Preparation of Acetic acid 4-[1-(3-fluoro-benzyl)-1H-indazol-5-ylamino]-pyrrolo[2,1-f][1,2,4]triazin-5-ylmethylester A solution of crude 5-bromomethyl-chloropyrrolo[2,1-f][1,2,4]triazine (15.3 gm, 0.062 mole) in EtOAc (300 mL) and cooled in an ice bath under a N₂ atmosphere and acetic acid (17.8 mL, 5 equiv) followed by diisopropylethylamine (54.3 mL, 5 equiv.) were added. The reaction vessel was removed from the bath and stirred for 18 hours at RT. The precipitate was removed by filtration and the resulting filtrate was diluted with hexane (250 mL). This was washed with water (2×125 mL), saturated NaCl solution (50 mL), dried (Na₂SO₄), and concentrated in vacuo to give a viscous brown oil which solidify on standing. A sample of pure acetic acid 4-chloro-pyrrolo[2,1-f][1,2,4]triazin-5-ylmethyl ester was obtained by silica gel chromatography (gradient elution with 0 to 30% EtOAc in hexane) as a yellow crystalline solid. ¹H NMR (CDCl₃,) δ 2.09 (s, 3H), 5.48 (s, 2H), 7.00 (d, J=2.7 Hz, 1H), 7.80 (d, J=2.7 Hz, 1H), 8.18 (s, 1H), 7.80 (d, J=2.7 Hz, 1H), 7.00 (d, J=2.7 Hz, 1H), 5.48 (s, 2H), 2.09 (s, 3H). The crude acetic acid 4-chloro-pyrrolo[2,1-f][1,2,4]triazin-5-ylmethyl ester was then dissolved in acetonitrile (300 mL) and treated with sodium bicarbonate (26.2 gm, 5 equiv.) and (18.1 gm, 1.2 equiv.). After stirring at RT for 20 hr, the mixture was concentrated in vacuo and dissolved in DCM (500 mL). This was washed with 100 mL water, dried over anhydrous sodium sulfate, filtered and concentrated in vacuo to give a dark colored solid. This was crystallized from acetonitrile to give 10 g of the title compound. The mother liquor was chromatographed on silica gel eluting with 70% hexane/EtOAc to give another 8 gm of pure material (overall yield, 67%): ¹H NMR (CDCl₃) δ 2.16 (s, 3H), 5.42 (s, 2H), 5.59 (s, 2H), 6.76 (d, J=2.5 Hz, 1H), 6.84 (d, J=8.8 Hz, 1H), 6.98–6.90 (bm, 2H), 7.35–7.22 (bm, 3H), 7.56 (d, J=2.6 Hz, 1H), 7.65 (d, J=8.8 Hz, 1H), 7.96 (s, 1H), 8.06 (s, 1H), 8.17 (s, 1H), 9.42 (s, 1H); MS: 431 (M+H⁺); HPLC Ret Time=2.59 min (YMC Xterra 4.5×50 mm S7 C18 column, 3 min gradient, 4 mL/min).

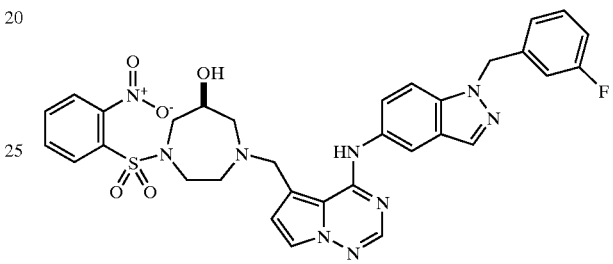

E. Preparation of 1-{4-[1-(3-Fluoro-benzyl)-1H-indazol-5-ylamino]-pyrrolo[2,1-f][1,2,4]triazin-5-ylmethyl}-4-(2-nitro-benzenesulfonyl)-(6S)-[1,4]diazepan-6-ol A mixture of acetic acid 4-[1-(3-fluoro-benzyl)-1H-indazol-5-ylamino]-pyrrolo[2,1-f][1,2,4]triazin-5-ylmethyl ester (860 mg, 2 mmole), 1-(2-nitro-benzenesulfonyl)-[1,4]diazepan-6R-ol (602 mg, 2 mmole) and diisopropylethylamine (0.522 mL, 3 mmole, 1.5 equiv.) in dry acetonitrile (4 ml) in a pressure vessel was heated at 102° C. for 17 hours. After removal of the solvent, the residue was taken up in DCM, washed with water, and dried (Na₂SO₄). Removal of the solvent followed by silica gel chromatography (gradient elution with DCM containing 0 to 2% 2M NH₃ in MeOH) afforded the title compound as a solid (1.14 g, 85%). ¹H NMR (CDCl₃) δ 2.87–3.08 (m, 5H), 3.36–3.60 (m, 4H), 3.97–4.05(m, 3H), 5.52 (s, 2H), 6.51 (d, 1J=2.5 Hz), 6.82 (m, 1H), 6.91–6.96 (m, 2H), 7.21–7.25 (m, 1H), 7.25–7.31 (m, 1H), 7.44 (d, 1H, J=3.0 Hz), 7.47–7.49 (m, 1H), 7.58–7.66 (m, 3H), 7.85 (s, 1H), 7.91 (d, 1H, J=1.5 Hz), 7.98 (d, 1H, J=1.0 Hz), 8.03 (d, 1H, J=1.5 Hz), 11.02 (s, 1H). MS: 672 (M+H⁺); HPLC Ret Time: 1.37 min (Gradient Time=2 min, Flow Rate=5 ml/min, Xterra C18 S7, 3.0×50 mm C18 S7 column).

F. Preparation of 1-{4-[1-(3-Fluoro-benzyl)-1H-indazol-5-ylamino]-pyrrolo[2,1-f][1,2,4]triazin-5-ylmethyl}-(6R)-[1,4]diazepan-6-ol Benzenethiol (54 mg, 2 equiv) was added to a suspension of 1-{4-[1-(3-fluoro-benzyl)-1H-indazol-5-ylamino]-pyrrolo[2,1f][1,2,4]triazin-5-ylmethyl}-4-(2-niro-benzenesulfonyl)-(6S)-[1,4]diazepan-6-ol (164 mg, 0.244 mmole) and K₂CO₃ (168 mg, 1.22 mmole, 5 equiv.) in 2.5 ml of anhydrous DMF under nitrogen. After stirring at RT for 50 min, the solid was removed by filtration. The filtrate was concentrated and partitioned between DCM and water.

The organic phase was dried (Na₂SO₄) and the solvent removed. Radial chromatography (2 mm silica gel plate, gradient elution with 0 to 5% 2M NH₃ in MeOH) afforded the title compound as a solid (109 mg, 92%). ¹H NMR (CDCl₃) δ 2.69–2.77 (m, 2H), 2.84–3.03 (m, 6H), 3.78–3.81 (m, 1H), 3.90 (d, 1H, J=13.4 Hz), 3.96 (d, 1H, J=13.4 Hz), 5.55 (s, 2H), 6.48 (d, 1H, J=2.5 Hz), 6.86–6.88 (m, 1H), 6.92–6.98 (m, 2H), 7.23–7.27 (m, 1H), 7.32–7.33 (m, 1H), 7.44 (d, 1H, 2.5 Hz), 7.54–7.56 (m, 1H), 7.86 (s, 1H), 8.02 (d, 1H, J=1.0 Hz), 8.04 (d, 1H, J=2.0 Hz), 11.54 (s, 1H). MS: 487 (M+H)⁺; HPLC Ret Time: 18.86 min (Chiralpak AD 4.6×250 mm column, eluting with 0.05% diethylamine in EtOH for 25 min with a flow rate of 0.7 mL/min).

EXAMPLE 79

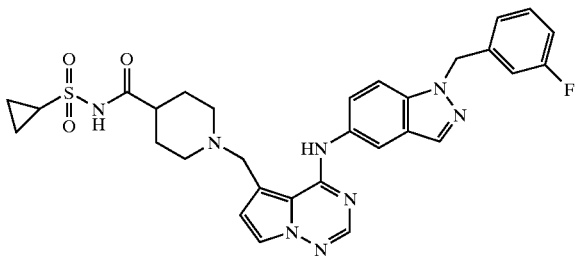

Cyclopropanesulfonic acid (1-{4-[1-(3-fluoro-benzyl)-1H-indazol-5-ylamino]-pyrrolo[2,1-f][1,2,4]triazin-5-ylmethyl}-piperidine-4-carbonyl)-amide Aqueous NaOH (2.1 mL, 1.0 N) was added to a solution of 1-{4-[1-(3-fluoro-benzyl)-1H-indazol-5-ylamino]-pyrrolo[2,1-f][1,2,4]triazin-5-ylmethyl}-piperidine-4-carboxylic acid methyl ester (352 mg, 0.686 mmole) in a mixture of MeOH (0.2 ml) and THF (0.2 ml) at 0° C. After stirring at 0° C. for 1 hour, the reaction mixture was allowed to warm to RT and left stirring overnight. Aqueous HCl (2.1 ml, 1.0 N) was added dropwise and the reaction was extracted with DCM. The organic extracts were dried (Na₂SO₄) and the solvents were removed to leave 1-{4-[1-(3-fluoro-benzyl)-1H-indazol-5-ylamino]-pyrrolo[2,1-f][1,2,4]triazin-5-ylmethyl}-piperidine-4-carboxylic acid, as a solid (329 mg, purity 84% by LCMS) which was used as such. A solution of the crude acid (100 mg, 0.168 mmole) in THF (2 ml) was added dropwise to a solution of 1,1'-carbonyldiimidazole (33 mg, 0.2 mmole) in THF (0.3 ml) and this was heated at reflux for 30 min. After cooling to RT, cyclopropylsulfonamide (82 mg, 0.67 mmole, 4 equiv.) was added followed by a solution of DBU (50 uL, 0.336 mmole, 2 equiv.) in THF (0.2 ml). The reaction was stirred for 18 hr, diluted with EtOAc (120 ml), washed with pH 4.0 buffer (9 mL), brine (5 mL) and dried (Na₂SO₄). Removal the solvent followed by radial chromatography (2 mm silica gel plate gradient elution with DCM containing 1 to 5% MeOH) afforded the title compound as a solid (58 mg, 57%). ¹H NMR (CDCl₃) δ 0.98–1.00 (m, 2H), 1.22–1.27 (m, 2H), 1.84–1.92 (m, 4H), 2.03–2.16 (m, 2H), 2.24–2.3 (m, 1H), 2.83–2.92 (m, 1H), 3.08–3.11 (m, 2H), 3.74 (s, 2H), 5.54 (s, 2H), 6.46 (d, 1H, J=2.5 Hz), 6.81–6.97 (m, 3H), 7.20–7.27 (m, 1H), 7.36–7.51 (m, 3H), 7.84 (s, 1H), 8.06 (s, 1H), 11.82 (bs, 1H). MS: 603.7 (M+H⁺); HPLC Ret Time: 1.21 min (Gradient Time=2 min, Flow Rate=5 ml/min, Xterra 3.0×50 mm S7 C18 column).

EXAMPLE 80

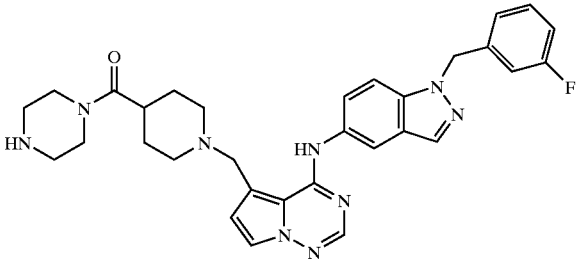

(1-{4-[1-(3-Fluoro-benzyl)-1H-indazol-5-ylamino]-pyrrolo[2,1-f][1,2,4]triazin-5-ylmethyl}-piperidin-4-yl)-piperazin-1-yl-methanone A mixture of crude 1-{4-[1-(3-fluoro-benzyl)-1H-indazol-5-ylamino]-pyrrolo[2,1-f][1,2,4]triazin-5-ylmethyl}-piperidine-4-carboxylic acid (75 mg, 0.15 mmole), EDC (72 mg, 0.376 mmole), and DMAP (37 mg, 0.3 mmole) in dry DCM (1 mL) was stirred at RT for 0.5 hr. Piperazine (104 mg, 1.2 mmole) was added and, after 64 hr, the reaction was diluted with DCM, washed with water and dried (Na₂SO₄). Removal of solvent followed by radial chromatography (1 mm silica gel plate, gradient elution with DCM containing 1 to 5% MeOH) afforded the title compound as a solid (11 mg, 13%). ¹H NMR (CDCl₃) δ 1.67–1.80 (m, 4H), 1.96–2.09 (m, 2H), 2.15–2.18 (m, 1H), 2.58–2.65 (m, 1H), 2.82–2.86 (m, 4H), 3.17–3.20 (m, 2H), 3.43–3.48 (m, 2H), 3.57–3.62 (m, 2H), 3.77 (s, 2H), 5.57 (s, 2H), 6.48 (d, 1H, J=2.5 Hz), 6.83–6.88 (m, 1H), 6.90–6.97 (m, 2H), 7.21–7.29 (m, 1H), 7.36–7.39 (m, 1H), 7.44 (d, 1H, J=2.7 Hz), 7.55–7.58 (m, 1H), 7.89 (s, 1H), 8.08 (s, 1H), 8.18 (d, 1H, J=1.5 Hz), 11.87 (br, 1H). MS: 568.67 (M+H⁺); HPLC Ret Time: 1.03 min (Gradient Time=2 min, Flow Rate=5 ml/min, Xterra 3.0×50 mm S7 C18 column).

EXAMPLE 81

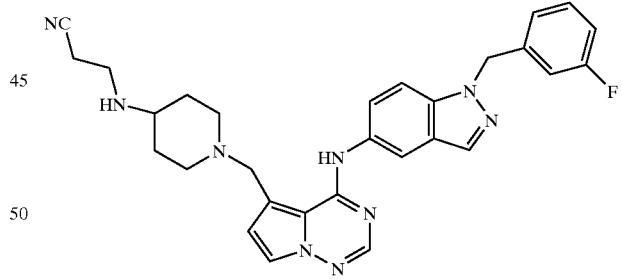

3-(1-{4-[1-(3-Fluoro-benzyl)-1H-indazol-5-ylamino]-pyrrolo[2,1-f][1,2,4]triazin-5-ylmethyl}-piperidin-4-ylamino)-propionitrile Acrylonitrile (0.2 mL, 30 equiv.) was added to a solution of [5-(4-amino-piperidin-1-ylmethyl)-pyrrolo[2,1-f][1,2,4]triazin-4-yl]-[1-(3-fluoro-benzyl)-1H-indazol-5-yl]-amine (47 mg, 0.1 mmole) in MeOH (3 mL) at RT. Removal the solvent followed by radial chromatography (1 mm silica gel plate, gradient elution with DCM containing 0 to 2% MeOH) afforded 40 mg (76%) of the title compound as a solid. MS: 524 (M+H)⁺; HPLC Ret Time: 0.99 min (Xterra 3.0×50 mm S7 C18 column, 2 min gradient, 5 mL/min).

EXAMPLE 82

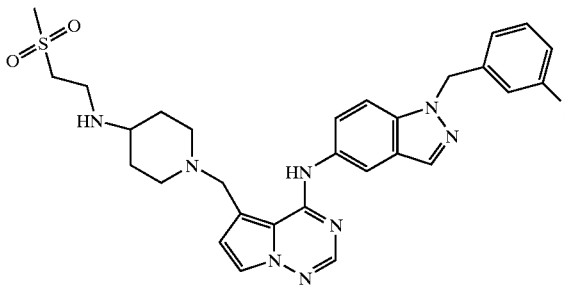

[1-(3-Fluoro-benzyl)-1H-indazol-5-yl]-{5-[4-(2-methanesulfonyl-ethylamino)-piperidin-1-ylmethyl]-pyrrolo[2,1-f][1,2,4]triazin-4-yl}-amine Methyl vinyl sulfone (0.011 mL, 0.1 mmole) was added to a solution of [5-(4-amino-piperidin-1-ylmethyl)-pyrrolo[2,1-f][1,2,4]triazin-4-yl]-[3-fluoro-benzyl)-1H-indazol-5-yl]-amine (47 mg, 0.1 mmole) in MeOH (3 mL) at RT. After stirring overnight, the title compound title compound (54 mg, 94%) was collected by filtration washed with MeOH and dried. MS: 577 (M+H)$^+$; HPLC Ret Time: 0.98 min (Xterra 3.0×50 mm S7 C18 column, 2 min gradient, 5 ml/min).

EXAMPLE 83

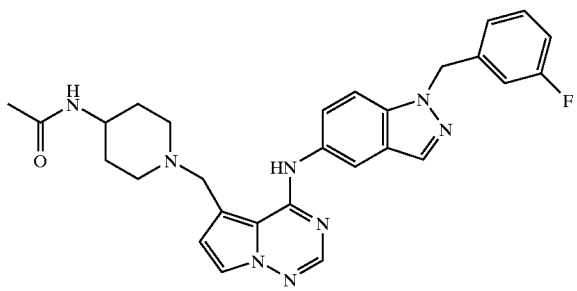

N-(1-{4-[1-(3-Fluoro-benzyl)-1H-indazol-5-ylamino]-pyrrolo[2,1-f][1,2,4]triazin-5-ylmethyl}-piperidin-4-yl)-acetamide Acetic anhydride (25 uL, 2.3 equiv.) was added to a mixture of [5-(4-amino-piperidin-1-ylmethyl)-pyrrolo[2,1-f][1,2,4]triazin-4-yl]-[1-(3-fluoro-benzyl)-1H-indazol-5-yl]-amine (47 mg, 0.1 mmole) and K$_2$CO$_3$ (21 mg 0.15 mmole) in MeOH (3 mL) at 0° C. under nitrogen. After 1 h, the reaction was removed from the ice bath and the mixture was left stirred at RT overnight. The solvent was removed and the residue was taken up in DCM, washed with water and dried (Na$_2$SO$_4$). Removal of the solvent followed by radial chromatography (2 mm silica gel plate, gradient elution with DCM containing 0 to 3% MeOH) afforded the title compound as a solid (41 mg, 80%). MS: 513 (M+H)$^+$; HPLC Ret Time: 1.12 min (Xterra 3.0×50 mm S7 C18 column, 2 min gradient, 5 mL/min).

EXAMPLE 84

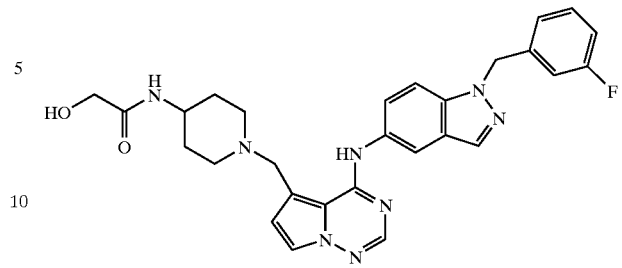

N-(1-{4-[1-(3-Fluoro-benzyl)-1H-indazol-5-ylamino]-pyrrolo[2,1-f][1,2,4]triazin-5-ylmethyl}-piperidin-4-yl)-2-hydroxy-acetamide Acetoxyacetyl chloride (46 mg, 2 equiv) was added dropwise to a solution of [5-(4-amino-piperidin-1-ylmethyl)-pyrrolo[2,1-f][1,2,4]triazin-4-yl]-[1-(3-fluoro-benzyl)-1H-indazol-5-yl]-amine (47 mg, 0.1 mmole) (80 mg, 0.17 mmole) and triethylamine (71 µL, 3 equiv.) in dry DCM (3 mL) at 0° C. under nitrogen. After stirring at 0° C. for 3 hr and at RT for 1 hr, it was diluted with DCM, washed with water and dried (Na$_2$SO$_4$). Removal of the solvent followed by radial chromatography (2 mm silica gel plate, gradient elution with DCM containing 0 to 2% MeOH) afforded acetic acid (1-{4-[1-(3-fluoro-benzyl)-1H-indazol-5-ylamino]-pyrrolo[2,1-f][1,2,4]triazin-5-ylmethyl}-piperidin-4-ylcarbamoyl)-methyl ester as a solid (73 mg, 75%). A solution of this ester in THF (0.4 mL) was treated with aq. NaOH (IN, 0.38 mL, 3 equiv.). After 2 hr at RT it was diluted with DCM, washed with water and dried (Na$_2$SO$_4$). Removal of the solvent followed by radial chromatography (2 mm silica gel plate employing gradient elution with DCM containing 0 to 3% MeOH) afforded the title compound as a solid (47 mg, 70%). MS: 529 (M+H)$^+$; HPLC Ret Time: 1.37 min (YMC Xterra ODS S7 3.0×50 mm column, 2 min gradient, 5 ml/min).

EXAMPLE 85

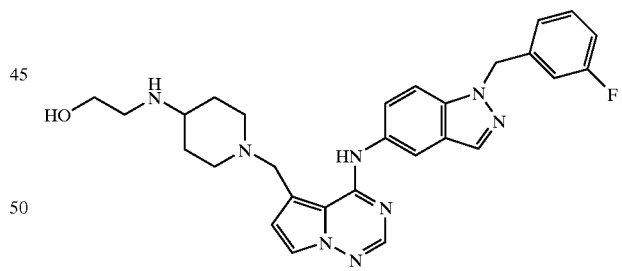

2-(1-{4-[1-(3-Fluoro-benzyl)-1H-indazol-5-ylamino]-pyrrolo[2,1-f][1,2,4]triazin-5-ylmethyl}-piperidin-4-ylamino)-ethanol A mixture of [5-(4-amino-piperidin-1-ylmethyl)-pyrrolo[2,1-f][1,2,4]triazin-4-yl]-[1-(3-fluoro-benzyl)-1H-indazol-5-yl]-amine (188 mg, 0.4 mmole) and [1,3]dioxolan-2-one (352 mg, 10 equiv) in a sealed tube was heated at 100° C. for 3.5 h. The title compound was isolated by radial chromatography (2 mm silica gel plate, gradient elution with DCM containing 0 to 3% MeOH) afforded the title compound as a solid (43 mg, 21%); MS: 515 (M+H$^+$); HPLC Ret Time: 1.29 min (YMC Xterra ODS S7 3.0×50 mm column, 2 min gradient, 5 ml/min).

EXAMPLE 86

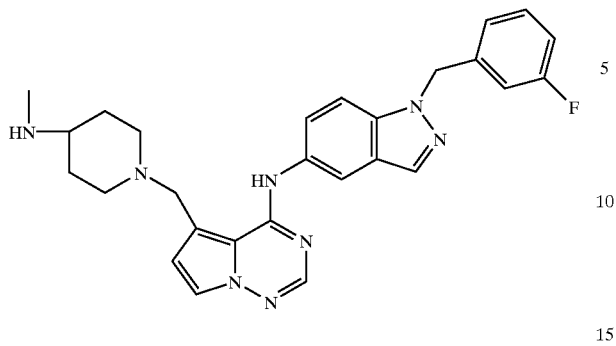

[1-(3-Fluoro-benzyl)-1H-indazol-5-yl]-[5-(4-methylamino-piperidin-1-ylmethyl)-pyrrolo[2,1-f][1,2,4]triazin-4-yl]-amine A mixture of (5-benzenesulfinylmethyl-pyrrolo[2,1-f][1,2,4]triazin-4-yl)-[1-(3-fluoro-benzyl)-1H-indazol-5-yl]-amine (200 mg, 0.4 mmole) and 4-amino-piperidine (1.2 g, 30 equiv.) in a vial was placed in microwave reactor (Personal Chemistry's Smith Creator) and irradiated at 150° C. for 20 min. Ethyl formate (3 ml) was added to above mixture and irradiation was continued at 135° C. for 30 min. Concentration of the reaction mixture followed by preparative HPLC purification afforded N-(1-{4-[1-(3-fluoro-benzyl)-1H-indazol-5-ylamino]-pyrrolo[2,1-f][1,2,4]triazin-5-ylmethyl}-piperidin-4-yl)-formamide (71 mg, 36%). This was dissolved in dry THF (0.3 ml) and added dropwise to a stirred solution of LiAlH$_4$ (1M in ether, 0.57 ml, 4 equiv.). Water (0.5 mL) was slowly added after 20 hr and the title compound (16 mg, 23%) was isolated by preparative HPLC. MS: 485 (M+H)$^+$; HPLC Ret Time: 1.02 min (Xterra 3.0×50 mm S7 C18 column, 2 min gradient, 5 ml/min).

EXAMPLE 87

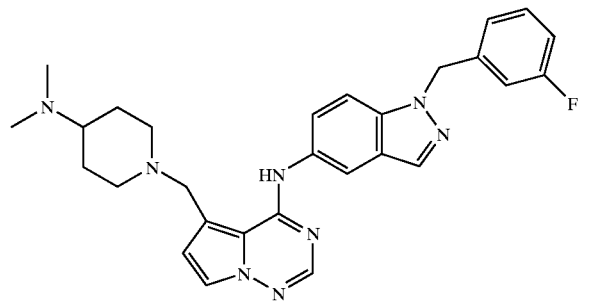

[5-(4-Dimethylamino-piperidin-1-ylmethyl)-pyrrolo[2,1-f][1,2,4]triazin-4-yl]-[1-(3-fluoro-benzyl)-1H-indazol-5-yl]-amine Sodium cyanoborohydride (5 mg, 2 equiv.) was added to a solution of [5-(4-amino-piperidin-1-ylmethyl)-pyrrolo[2,1-f][1,2,4]triazin-4-yl]-[1-(3-fluoro-benzyl)-1H-indazol-5-yl]-amine (20 mg, 0.042 mmole), acetic acid (3 uL), and 37% formaldehyde (7 uL, 2 equiv.) in DCM (0.3 ml) at 0° C. After 0.5 h, the reaction was removed from the ice-bath and, after an additional 4 h, was diluted with DCM and made alkaline with saturated NaCO$_3$ solution. The organic layer was dried (Na$_2$SO$_4$) and the solvent was removed. The title compound (4 mg, 8%) was isolated by preparative HPLC. MS: 499 (M+H)$^+$; HPLC Ret Time: 1.04 min (YMC ODS-A C18 S7 3.0×50 mm column, 2 min gradient, 5 ml/min).

EXAMPLE 88

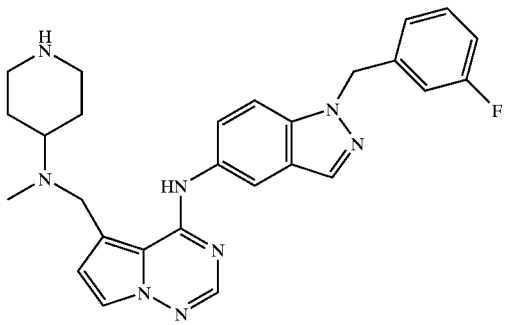

[1-(3-Fluoro-benzyl)-1H-indazol-5-yl]-{5-[(methyl-piperidin-4-yl-amino)-methyl]-pyrrolo[2,1-f][1,2,4]triazin-4-yl}-amine Similarly, 4-({4-[1-(3-fluoro-benzyl)-1H-indazol-5ylamino]-pyrrolo[2,1-f][1,2,4]triazin-5-ylmethyl}-amino)-piperidin-1-carboxylic acid tert-butyl ester was convertet to 4-({4-[1-(3-fluoro-benzyl)-1H-indazol-5-ylamino]-pyrrolo[2,1-f][1,2,4]triazin-5-ylmethyl}-methylamino)-piperidin-1-carboxylic acid tert-butyl ester which was treated with TFA at 0° C. for 1 h to give the title compound as a solid (overall yield 37%). MS: 485 (M+H)$^+$; HPLC Ret Time: 0.95 min (YMC 3.0×50 mm S7 C18 column, 2 min gradient, 5 ml/min).

EXAMPLE 89

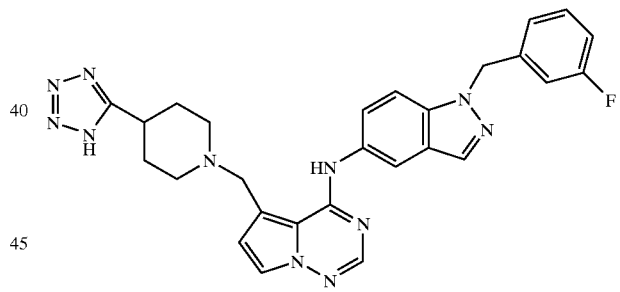

[1-(3-Fluoro-benzyl)-1H-indazol-5-yl]-{5-[4-(1H-tetrazol-5-yl)-piperdin-1-ylmethyl]-pyrrolo[2,1-f][1,2,4]triazin-4-yl}-amine A mixture of 1-{4-[1-(3-fluoro-benzyl)-1H-indazol-5-ylamino]-pyrrolo[2,1-f][1,2,4]triazin-5-ylmethyl}-piperidine-4-carbonitrile (145 mg, 0.3 mmole), sodium azide (59 mg, 3 equiv.) and ammonium chloride (48 mg, 3 equiv.) in DMF (0.6 mL) in a sealed vial was stirred at 100° C. for 20 h. The reaction mixture was cooled to RT, diluted with DCM, washed with water, and dried (Na$_2$SO$_4$). Removal the solvent followed by radial chromatography (2 mm silica gel plate, gradient elution with DCM containing 2 to 7% 2 M NH$_3$ in MeOH) afforded the title compound as a solid (38 mg, 24%); MS: 524 (M+H$^+$); HPLC Ret Time: 1.13 min (Xterra 3.0×50 mm S7 C18 column, 2 min gradient, 5 ml/min).

EXAMPLE 90

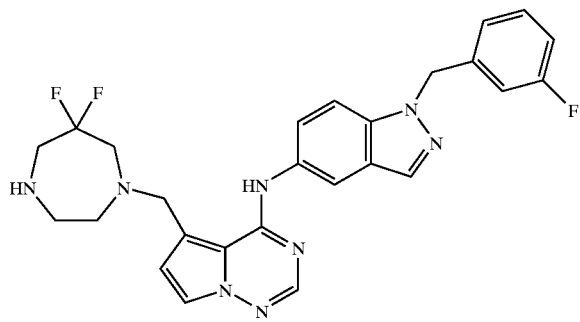

[5-(6,6-Difluoro-[1,4]diazepan-1-ylmethyl)-pyrrolo[2,1-f][1,2,4]triazin-4-yl]-[1-(3-fluoro-benzyl)-1H-indazol-5-yl]-amine

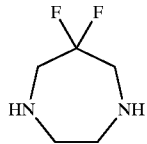

A. Preparation of 6,6-Difluoro-[1,4]diazepane

Tertrapropylammonium perruthenate (0.75 gm, 0.05 equiv) was added to a stirred suspension of 1,4-bis-(toluene-4-sulfonyl)-[1,4]diazepan-6-ol (13 gm, 30.7 mmoles, Saari et al., J. Org. Chem., 1971, 36, 1711), N-methylmorpholine N-oxide (5.38 gm, 1.5 equiv) and crushed 4 A molecular sieves (20 gm) in dry DCM (100 mL). After 1.5 hr, this was poured onto a short column of silica gel and eluted with a mixture of 10% EtOAc in DCM to give 1,4-bis-(toluene-4-sulfonyl)-[1,4]diazepan-6-one (8.9 gm, 60%) as a white solid: $^1$H NMR (CDCl$_3$) δ 2.44 (s, 6H), 3.71 (s, 4H), 3.91 (s, 4H), 7.32 (d, 4H, J=8.1 Hz), 7.65 (d, 4H, J=8.1 Hz). A solution of this ketone (8.9 gm, 21.1 mmole) in dry DCM was cooled in an acetone/dry ice bath and DAST (8.4 mL, 3 equiv) was added over 5 min. The reaction was allowed to warm to RT and, after 20 hr, it was cooled in an ice bath and water was added dropwise to decompose the excess reagent. The pH of the aqueous phase was adjusted to 10 with aq. NaOH solution and additional DCM (300 mL) was added. The organic phase was separated, dried (Na2SO4) and the solvent removed. The residue was crystallized from acetone/water to give 6,6-difluoro-1,4-bis-(toluene-4-sulfonyl)-[1,4] diazepane (6.47 gm, 69%) as fluffy white crystals: $^1$H NMR (CDCl$_3$) δ 2.44 (s, 6H), 3.41 (s, 4H), 3.68 (t, 4H, J=12.3 Hz), 7.33 (d, 4H, J=8.0 Hz), 7.64 (d, 4H, J=8.0 Hz). A solution of the difluoride (3.41 gm, 7.75 mmole) and phenol (2.9 gm, 4 equiv) in a 30% solution of HBr in HOAc (50 mL) was heated at 60° C. for 6 hr. The reaction was concentrated and the residue was suspended in ethanol to deposit the bis-HBr salt of 6,6-difluoro-[1,4]diazepane as a tan solid (1.82 gm, 79%). This salt (600 mg, 2.04 mmole) was suspended in MeOH (10 mL) and aq. NaOH (0.41 mL, 10 N, 2 equiv) was added with stirring. The resulting solution was eluted through a Varian Mega Bond Elut SCX cartridge followed by 10 mL of MeOH. 6,6-Difluoro-[1,4]diazepane was eluted off the SCX cartridge with 50 mL of 2 N solution of NH3 in MeOH. Removal of the solvents left it as an oil (211 mg, 76%): $^1$H NMR (CDCl$_3$) δ 2.93 (s, 4H), 3.21 (t, 4H, J=13.9 Hz).

B. Preparation of [5-(6,6-Difluoro-[1,4]diazepan-1-ylmethyl)-pyrrolo[2,1-f][1,2,4]triazin-4-yl]-[1-(3-fluoro-benzyl)-1H-indazol-5-yl]-amine A solution of methanesulfonic anhydride (114 mg, 3.2 equiv.) in DCM (0.6 mL) was added to a solution of {4-[1-(3-fluoro-benzyl)-1H-indazol-5-ylamino]-pyrrolo[2,1-f][1,2,4]triazin-5-yl}-methanol (78 mg, 2 mmole) in dry DCM (1.4 mL) at 0° C. under nitrogen followed by triethylamine (0.140 mL, 5 equiv.). After stirring at 0° C. for 1 hr, 6,6-difluoro-[1,4]diazepane (82 mg, 3 equiv.) and 1,2 dichloroethane (2 mL) were added. The reaction mixture was transferred to a microwave reactor (Personal Chemistry's Smith Creator) and irradiated at 65° C. for 50 min. Removal of the solvent followed by preparative HPLC afforded the title compound as a solid (29 mg, 29%). MS: 507 (M+H$^+$); HPLC Ret Time: 1.47 min (YMC Xterra ODS S7 3.0x50 mm column, 2 min gradient, 5 ml/min).

EXAMPLE 91

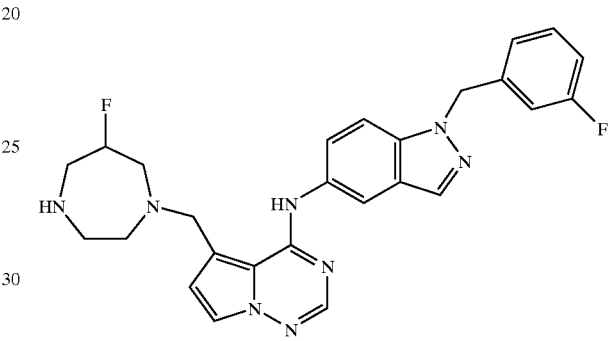

(±)-[1-(3-Fluoro-benzyl)-1H-indazol-5-yl]-[5-(6-fluoro-[1,4]diazepan-1-ylmethyl)-pyrrolo[2,1-f][1,2,4]triazin-4-yl]-amine Following the above coupling procedure with 6-fluoro-[1,4]diazepane (Ziegler et al., J. Med. Chem., 1990, 33, 142) gave the title compound as a solid (yield 26%). MS: 489 (M+H)$^+$; HPLC Ret Time: 1.33 min (YMC Xterra ODS S7 3.0x50 mm column, 2 min gradient, 5 ml/min).

EXAMPLE 92

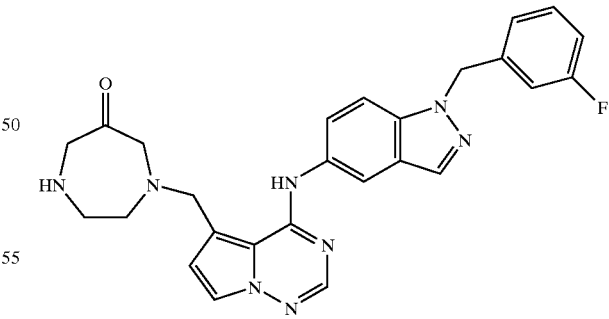

1-{4-[1-(3-Fluoro-benzyl)-1H-indazol-5-ylamino]-pyrrolo[2,1-f][1,2,4]triazin-5-ylmethyl}-[1,4]diazepan-6-one Oxidation of 4-{4-[1-(3-fluoro-benzyl)-1H-indazol-5-ylamino]-pyrrolo[2,1-f][1,2,4]triazin-5-ylmethyl}-6-hydroxy-[1,4]diazepane-1-carboxylic acid tert-butyl ester as described for Example 74 gave 4-{4-[1-(3-fluoro-benzyl)-1H-indazol-5-ylamino]-pyrrolo[2,1-f][1,2,4]triazin-5- ylmethyl}-6-oxo-[1,4]diazepane-1-carboxylic acid tert-butyl ester which was deprotected with TFA to afford the title compound as a solid (overall yield 61%). MS: 485 (M+H)+; HPLC Ret Time: 1.01 min (Xterra S7 3.0×50 mm S7 C18 column, 2 min gradient, 5 ml/min).

EXAMPLE 93

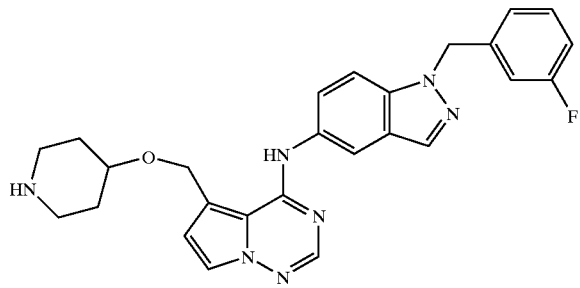

[1-(3-Fluoro-benzyl)-1H-indazol-5yl]-[5-(piperidin-4-yloxymethyl)-pyrrolo[2,1-f][1,2,4]triazin-4-yl]-amine A suspension of 5-bromomethyl-4-chloro-pyrrolo[2,1-f][1,2,4]triazine (61 mg, 0.25 mmole), 4-hydroxy-piperidine-1-carboxylic acid tert-butyl ester (500 mg, 10 equiv) and NaHCO$_3$ (42 mg, 2 equiv) in dry CH$_3$CN (0.5 mL) under N$_2$ was left stirring at RT for 3 days. 1-(3-Fluoro-benzyl)-1H-indazol-5-ylamine (54 mg, 0.9 equiv) and additional NaHCO$_3$ (42 mg, 2 equiv) were added and the reaction was left stirring overnight. The reaction was diluted with DCM, washed with water, and dried (Na$_2$SO$_4$). Removal of the solvent followed by radial chromatography (2 mm silica gel plate, gradient elution with DCM containing 0 to 3% MeOH) afforded 4-{4-[1-(3-fluoro-benzyl)-1H-indazol-5-ylamino]-pyrrolo[2,1-f][1,2,4]triazin-5-ylmethoxy}-piperidine-1-carboxylic acid tert-butyl ester as a foam (47 mg, 33%). This was treated with a mixture of DCM (1.5 mL) and TFA (1 mL) for 40 min and then the solvents were removed. The residue was taken up in DCM, washed with sat. aq. NaHCO$_3$ solution, and dried (Na$_2$SO$_4$). Removal of the solvent followed by radial chromatography (2 mm silica gel plate, gradient elution with DCM containing 0 to 5% MeOH) afforded the pure amine (11 mg, 29%) as an oil. $^1$H NMR (CDCl$_3$) δ 1.1–1.3 (m, 2H), 1.7–1.9 (m, 4H), 2.5–2.6 (m, 2H), 3.0–3.1 (m, 2H), 3.44 (d, 2H, J=7 Hz), 4.85 (s, 2H), 5.59 (s, 2H), 6.55 (d, 1H, J=2 Hz), 6.8–7.0 (m, 3H), 7.2–7.5 (m, 4H), 7.97 (s, 1H), 8.05 (s, 1H), 8.20 (d, 1H, J=2 Hz), 9.70 (s, 1H); MS: 486 (M+H)+; HPLC Ret Time: 1.35 min (YMC S7 C18, 3.0×50 mm, 2 min gradient, 5 mL/min.

EXAMPLES 94 to 116

The follow ether analogs were prepared using the procedure described for Example 93. When the starting alcohol did not carry a Boc protecting group, the deprotection step was omitted. Alcohols that that carried a primary or secondary amino group were first converted to their N-Boc derivative using di-tert-butyl dicarbonate according to general literature procedures (T. Greene and P. Wuts, Protective Groups in Organic Synthesis, 3$^{rd}$ edition).

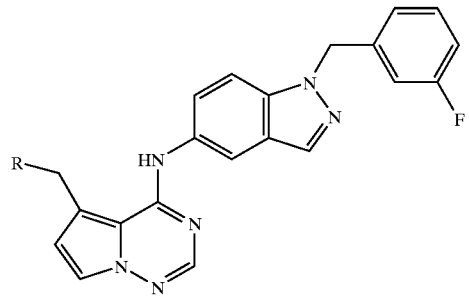

| Ex. | R | Compound Name | HPLC Ret Time (min) |
|---|---|---|---|
| 94 | MeO⌒⌒O | [1-(3-Fluoro-benzyl)-1H-indazol-5-yl]-[5-(2-methoxy-ethoxymethyl)-pyrrolo[2,1-f][1,2,4]triazin-4-yl]-amine | 1.33* |
| 95 | MeO | [1-(3-Fluoro-benzyl)-1H-indazol-5-yl]-(5-methoxymethyl-pyrrolo[2,1-f][1,2,4]triazin-4-yl)-amine | 2.18** |
| 96 | Me$_2$N⌒⌒O | [5-(2-Dimethylamino-ethoxymethyl)-pyrrolo[2,1-f][1,2,4]triazin-4-yl]-[1-(3-fluoro-benzyl)-1H-indazol-5-yl]-amine | 1.24 |
| 97 | imidazolyl-propoxy | [1-(3-Fluoro-benzyl)-1H-indazol-5-yl]-[5-(3-imidazol-1-yl-propoxymethyl)-pyrrolo[2,1-f][1,2,4]triazin-4-yl]-amine | 1.33 |
| 98 | HO⌒⌒O | 2-{4-[1-(3-Fluoro-benzyl)-1H-indazol-5-ylamino]-pyrrolo[2,1-f][1,2,4]triazin-5-ylmethoxy}-ethanol | 1.4 |

-continued

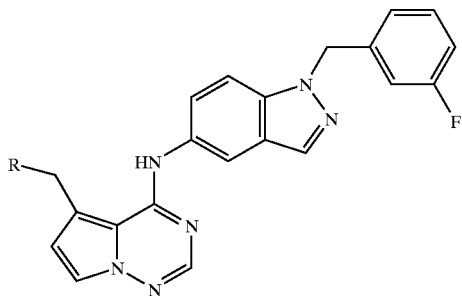

| Ex. | R | Compound Name | HPLC Ret Time (min) |
|---|---|---|---|
| 99 | HO, HO, O (racemic) | 3-{4-[1-(3-Fluoro-benzyl)-1H-indazol-5-ylamino]-pyrrolo[2,1-f][1,2,4]triazin-5-ylmethoxy}-propane-1,2-diol | 1.33 |
| 100 | HO~N(H)~O | 2-(2-{4-[1-(3-Fluoro-benzyl)-1H-indazol-5-ylamino]-pyrrolo[2,1-f][1,2,4]triazin-5-ylmethoxy}-ethylamino)-ethanol | 1.25 |
| 101 | (2S)-pyrrolidin-CH2-O | [1-(3-Fluoro-benzyl)-1H-indazol-5-yl]-[5-(2S)-pyrrolidin-2-ylmethoxymethyl)-pyrrolo[2,1-f][1,2,4]triazin-4-yl]-amine | 1.27 |
| 102 | (2R)-pyrrolidin-CH2-O | [1-(3-Fluoro-benzyl)-1H-indazol-5-yl]-[5-(2R)-pyrrolidin-2-ylmethoxymethyl)-pyrrolo[2,1-f][1,2,4]triazin-4-yl]amine | 1.27 |
| 103 | H2N-(2R)-CH(CH3)-CH2-O | [5-{(2R)2-Amino-propoxymethyl}-pyrrolo[2,1-f][1,2,4]triazin-4-yl]-[1-(3-fluoro-benzyl)-1H-indazol-5-yl]-amine | 1.33 |
| 104 | H2N-(2S)-CH(CH3)-CH2-O | [5-{(2S)-2-Amino-propoxymethyl}-pyrrolo[2,1-f][1,2,4]triazin-4-yl]-[1-(3-fluoro-benzyl)-1H-indazol-5-yl]-amine | 1.33 |
| 105 | H2N-CH2-CH2-O | [5-(2-Amino-ethoxymethyl)-pyrrolo[2,1-f][1,2,4]triazin-4-yl]-[1-(3-fluoro-benzyl)-1H-indazol-5-yl]-amine | 1.29 |
| 106 | piperidin-3-yl-CH2-O (racemic) | [1-(3-Fluoro-benzyl)-1H-indazol-5-yl]-[5-(piperidin-3-ylmethoxymethyl)-pyrrolo[2,1-f][1,2,4]triazin-4-yl]-amine | 1.34 |
| 107 | piperidin-2-yl-CH2-O (racemic) | [1-(3-Fluoro-benzyl)-1H-indazol-5-yl]-[5-(piperidin-2-ylmethoxymethyl)-pyrrolo[2,1-f][1,2,4]triazin-4-yl]-amine | 1.38 |

-continued

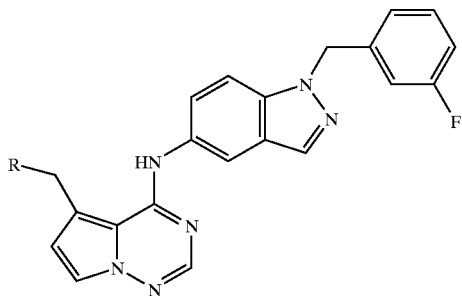

| Ex. | R | Compound Name | HPLC Ret Time (min) |
|---|---|---|---|
| 108 | HO~~~O (3-hydroxypropyloxy) | 3-{4-[1-(3-Fluoro-benzyl)-1H-indazol-5-ylamino]-pyrrolo[2,1-f][1,2,4]triazin-5-ylmethoxy}-propan-1-ol | 2.15** |
| 109 | (3S)-pyrrolidin-3-yloxy | [1-(3-Fluoro-benzyl)-1H-indazol-5-yl]-[5-{(3S)-pyrrolidin-3-yloxymethyl}-pyrrolo[2,1-f][1,2,4]triazin-4-yl]-amine | 1.24* |
| 110 | (3R)-pyrrolidin-3-yloxy | [1-(3-Fluoro-benzyl)-1H-indazol-5-yl]-[5-{(3R)-pyrrolidin-3-yloxymethyl}-pyrrolo[2,1-f][1,2,4]triazin-4-yl]-amine | 1.24* |
| 111 | piperidin-4-ylmethoxy | [1-(3-Fluoro-benzyl)-1H-indazol-5-yl]-[5-(piperidin-4-ylmethoxymethyl)-pyrrolo[2,1-f][1,2,4]triazin-4-yl]-amine | 1.35* |
| 112 | HO~~O~~OH (1,3-dihydroxypropan-2-yloxy) | 2-{4-[1-(3-Fluoro-benzyl)-1H-indazol-5-ylamino]-pyrrolo[2,1-f][1,2,4]triazin-5-ylmethoxy}-propane-1,3-diol | 1.41 |
| 113 | Me₂N~~~O | [5-(3-Dimethylamino-propoxymethyl)-pyrrolo[2,1-f][1,2,4]triazin-4-yl]-[1-(3-fluoro-benzyl)-1H-indazol-5-yl]-amine | 1.95*** |
| 114 | H₂N~~~~O | [5-(4-Amino-butoxymethyl)-pyrrolo[2,1-f][1,2,4]triazin-4-yl]-[1-(3-fluoro-benzyl)-1H-indazol-5-yl]-amine | 1.84**** |
| 115 | H₂N-CH₂-C(CH₃)₂-CH₂-O | [5-(3-Amino-2,2-dimethyl-propoxymethyl)-pyrrolo[2,1-f][1,2,4]triazin-4-yl]-[1-(3-fluoro-benzyl)-1H-indazol-5-yl]-amine | 2.12*** |
| 116 | H₂N~~~O | [5-(4-Amino-propoxymethyl)-pyrrolo[2,1-f][1,2,4]triazin-4-yl]-[1-(3-fluoro-benzyl)-1H-indazol-5-yl]-amine | 1.98*** |

Unless otherwise indicated, HPLC Retention Times were determined using a YMC Xterra ODS S7 3.0 × 50 mm column with a 2 minute gradient time and a flow rate of 5 mL/min. HPLC Retention Times marked with a "*" were determined using a YMC C18 SF 3.0 × 50 mm column with a 2 minute gradient time and a flow rate of 5 mL/min; with a "" were determined using using a YMC C18 SF 4.6 × 50 mm column with a 3 minute gradient time and a flow rate of 4 mL/min; with a "*" on a YMC Xterra C18 S5 4.6 × 50 mm column with a 3 min gradient time and a flow rate of 4 mL/min, with; with a "****" on a YMC Xterra C18 S5 3.0 × 50 mm column with a 3 min gradient and a flow rate of 4 mL/min.

EXAMPLE 117

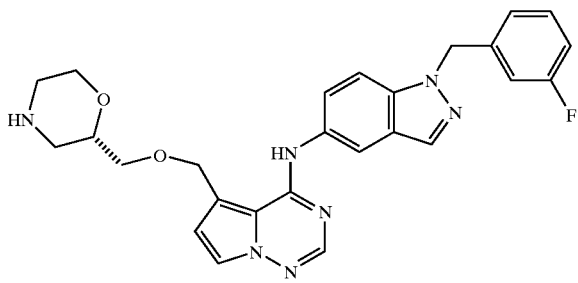

([1-(3-Fluoro-benzyl)-1H-indazol-5-yl]-[5-({2S}-morpholin-2-ylmethoxymethyl)-pyrrolo[2,1-f][1,2,4]triazin-4-yl]-amine

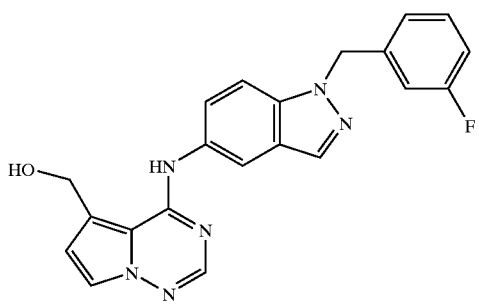

A. Preparation of {4-[1-(3-Fluoro-benzyl)-1H-indazol-5-ylamino]-pyrrolo[2,1-f][1,2,4]triazin-5-yl}-methanol A mixture of crude 5-bromomethyl-4-chloro-pyrrolo[2,1-f][1,2,4]triazine (3.69 gm, 0.015 moles and NaHCO₃ (2.51 gm, 2 equiv) in a mixture of acetonitrile (50 mL) and water (5 mL) was stirred under a N₂ atmosphere for 3 days. This was treated with Na₂SO₄ and then with 1-(3-flurobenzyl)-1H-indazol-5-ylamine (3.24 gm, 0.90 equiv) and NaHCO₃ (1 gm) and left stirring for 18 hr at RT. The reaction was filtered and the filter cake was washed with DCM (100 mL). The filtrate was concentrated and silica gel chromatography (elution with 30% EtOAc in hexane) of the residue gave the title compound as a tan solid (3.78 gm, 65% yield): ¹H NMR (CDCl₃) δ 3.03 (t, J=5.9 Hz, 1H), 4.98 (d, J=5.7 Hz, 2H), 5.55 (s, 2H), 6.76 (d, J=2.7 Hz, 1H), 6.83 (d, J=9.0 Hz, 1H), 6.98–6.90 (m, 3H), 7.43 (d, J=2.5 Hz, 1H), 7.51 (dd, J=2.1, 8.8 Hz, 1H), 7.96 (s, 1H), 8.03 (s, 1H), 8.22 (s, 1H), 9.91 (s, 1H); MS: (M+H+); HPLC Ret Time: 2.38 min (YMC C18 S5, 3.0×50 mm, 4 min gradient, 4 mL/min.

B. Preparation of ([1-(3-Fluoro-benzyl)-1H-indazol-5-yl]-[5-({2S}-morpholin-2-ylmethoxymethyl)-pyrrolo[2,1-f][1,2,4]triazin-4-yl]-amine Thionyl chloride (18 µL, 1.1 equiv) was added to a solution of {4-[1-(3-Fluoro-benzyl)-1H-indazol-5-ylamino]-pyrrolo[2,1-f][1,2,4]triazin-5-yl}-methanol (80 mg, 0.205 mmole) in dry DCM (4 mL) at RT. After 12 min, (2S)-2-hydroxymethyl-morpholine-4-carboxylic acid tert-butyl ester (65.3 mg, 1.5 equiv, H. Yanagisawa et al., Heterocycles, 1993, 35, 105.) was added followed by DIPEA (39.5 µL, 1.1 equiv). After 72 hr at RT, the solvent was removed and silica gel chromatography of the residue (gradient elution with 0 to 50% EtOAc in hexane) afforded 2-{4-[1-(3-Fluoro-benzyl)-1H-indazol-5-ylamino]-pyrrolo[2,1-f][1,2,4]triazin-5-ylmethoxymethyl}-morpholine-4-carboxylic acid tert-butyl ester (60 mg, 50% yield); MS: 588 (M+H)⁺; HPLC Ret Time: 2.69 min (Xterra C18 S5, 3.0×50 mm, 3 min gradient, 4 mL/min. A solution of this material in DCM (2 mL) was cooled to 0° C. and treated with TFA (1 mL). After 90 min, the solvents were removed and the residue was dissolved in DCM. This was washed with saturated NaHCO₃ solution and the organic phase was dried (Na₂SO₄) and the solvents removed. Purification by preparative HPLC and then radial chromatography (1 mm silica gel plate, gradient elution with 0 to 3% NH₃ (2N in MeOH) in DCM gave the title compound (30 mg, 60% yield): ¹H NMR (CDCl₃) δ 2.84–2.58 (m, 4H), 3.65–3.35 (m, 4H) 3.65–3.35 (m, 4H), 4.87 (s, 2H), 5.58 (s, 2H), 6.54 (d, J=2.5 Hz, 1H), 6.83 (d, J=9.5 Hz, 1H), 6.98–6.90 (m, 2H), 7.32–7.20 (m, 3H), 7.48 (d, J=2.5 Hz, 1H), 7.58 (dd, J=1.8, 8.8 Hz, 1H), 7.94 (s, 1H), 8.19 (s, 1H), 9.58 (s, 1H); MS: 488 (M+H)⁺; HPLC Ret Time: 1.65 min (Xterra C18 S5, 3.0×50 mm, 3 min gradient, 4 mL/min).

EXAMPLE 118

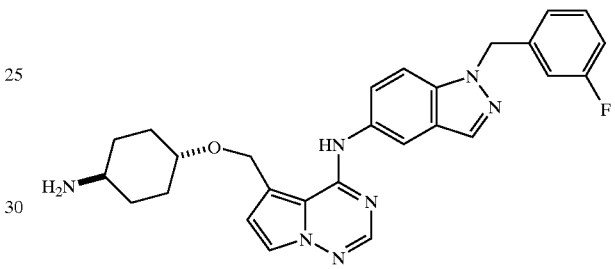

[trans-5-(4-Amino-cyclohexyloxymethyl)-pyrrolo[2,1-f][1,2,4]triazin-4-yl]-[1-(3-fluoro-benzyl)-1H-indazol-5-yl]-amine The title compound was prepared from (trans-4-hydroxy-cyclohexyl)-carbamic acid tert-butyl ester in a similar manner: MS: 486 (M+H)⁺; HPLC Ret Time: 2.13 min (Xterra C18 S5, 4.6×50 mm, 3 min gradient, 4 mL/min).

EXAMPLE 119

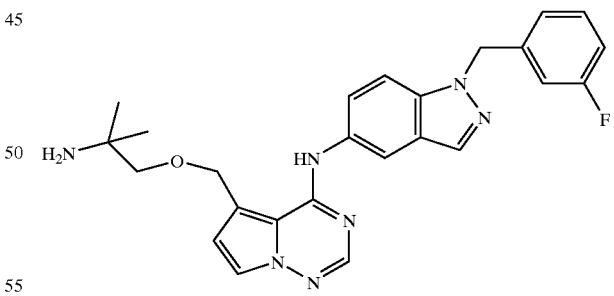

[5-(2-Amino-2-methyl-propoxymethyl)-pyrrolo[2,1-f][1,2,4]triazin-4-yl]-[1-(3-fluoro-benzyl)-1H-indazol-5-yl]-amine A mixture of acetic acid 4-[1-(3-fluoro-benzyl)-1H-indazol-5-ylamino]-pyrrolo[2,1-f][1,2,4]triazin-5-ylmethylester (100 mg, 0.24 mmol), (2-hydroxy-1,1-dimethyl-ethyl)-carbamic acid tert-butyl ester 156 mg, 3 equiv) and DIPEA (62 µL, 1.5 equiv) in dry acetonitrile (0.2 mL) in a vial was placed in a microwave reactor (Personal Chemistry's Smith Creator) and irradiated for 10 min at 109° C. The solvent was removed and the residue was taken up in dry DCM (3 mL) and cooled to 0° C. TFA (3 mL) was added and after 1.5 hr, the solvents were removed. The residue was partitioned between DCM and saturated NaHCO₃ solution. The organic phase was dried (Na₂SO₄) and the solvent was removed. Purification by radial chromatography (1 mm silica gel plate, gradient elution with 0 to 5% MeOH in DCM) gave the title compound (13 mg, 12% yield): MS: 460 (M+H)⁺; HPLC Ret Time: 1.34 min, YMC Xterra ODS S7 3.0×50 mm, 2 min gradient, 5 mL/min).

EXAMPLE 120

(1-Benzyl-1H-indazol-5-yl)-[5-(2-methoxy-ethoxymethyl)-pyrrolo[2,1-f][1,2,4]triazin-4-yl]-amine

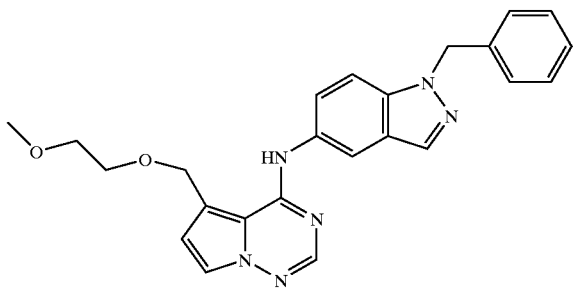

A suspension of 5-bromomethyl-4-chloro-pyrrolo[2,1-f][1,2,4]triazine (50 mg, 0.202 mmole and NaHCO₃ (75 mg, 4.4 equiv) in 2-methoxyethanol (1.0 mL) under N₂ was left stirring at RT for 6 hr. The reaction was diluted with DCM, extracted with water and dried (Na₂SO₄). Removal of the solvent left 4-chloro-5-(2-methoxy-ethoxymethyl)-pyrrolo[2,1-f][1,2,4]triazine (41 mg, 84%) as an oil. $^1$H NMR (CDCl₃) δ 3.40 (s, 3H), 3.67 (m, 4H), 4.96 (s, 2H), 7.05 (d, 1H, J=3 Hz), 7.82 (d, 1H, J=1 Hz), 8.16 (s, 1H). A suspension of 4-chloro-5-(2-methoxy-ethoxymethyl)-pyrrolo[2,1-f][1,2,4]triazine (5 mg, 0.020 mmole), NaHCO₃ (3 mg, 2 equiv) and 1-benzyl-1H-indazol-5-ylamine (4.5 mg, 1 equiv, prepared in the same manner as 1-(3-fluoro-benzyl)-1H-indazol-5-ylamine but using benzyl chloride) in dry CH₃CN (0.5 mL) was left stirring at RT for 2 hr. The reaction was diluted with DCM, washed with water and dried (Na₂SO₄). Removal of the solvent followed by radial chromatography (1 mm silica gel plate, gradient elution with DCM containing 0 to 1% MeOH) afforded the product as and oil (1.8 mg, 21%). $^1$H NMR (CDCl₃) δ 3.16 (s, 3H), 3.63 (m, 4H), 4.83 (s, 2H), 5.53 (s, 2H), 6.48 (d, 1H, J=3 Hz), 7.1–7.5 (m, 8H), 7.88 s, 1H), 7.96 (s, 1H), 8.11 (s, 1H), 9.56 (s, 1H); MS: 429 (M+H)⁺; HPLC Ret Time: 2.58 min (YMC C18 S5, 4.6×50 mm, 3 min gradient (starting with 0% solvent B and ending with 70% solvent B), 4 mL/min.

EXAMPLE 121

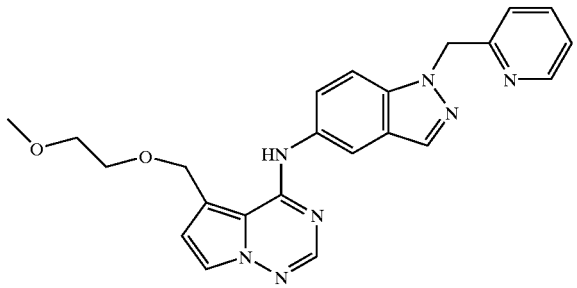

[5-(2-Methoxy-ethoxymethyl)-pyrrolo[2,1-f][1,2,4]triazin-4-yl]-(1-pyridin-2-ylmethyl-1H-indazol-5-yl)-amine A suspension of 4-chloro-5-(2-methoxy-ethoxymethyl)-pyrrolo[2,1-f][1,2,4]triazine (24 mg, 0.099 mmole), NaHCO₃ (42 mg, 5 equiv) and 1-pyridin-2-ylmethyl-1H-indazol-5-ylamine (22 mg, 1 equiv, prepared in the same manner as 1-(3-fluoro-benzyl)-1H-indazol-5-ylamine but using 2-picolyl chloride) in dry CH₃CN (1 mL) was left stirring at RT for 1 hr. The reaction was diluted with DCM, washed with water and dried (Na₂SO₄). Removal of the solvent followed by radial chromatography (1 mm silica gel plate, gradient elution with DCM containing 0 to 1% MeOH) afforded the product as and oil (4.8 mg, 11%). $^1$H NMR (CDCl₃) δ 3.26 (s, 3H), 3.76 (m, 4H), 4.90 (s, 2H), 5.75 (s, 2H), 6.56 (d, 1H, J=3 Hz), 6.83 (d, 1H, J=5 Hz), 7.18 (m, 1H), 7.40 (d, 1H, J=5 Hz), 7.49 (d, 1H, J=2 Hz), 7.56 (m, 2H), 7.96 (s, 1H), 8.07 (s, 1H), 8.22 (d, 1H, J=1 Hz), 8.59 (m, 1H), 9.65 (s, 1H); MS: 429 (M+H)+; HPLC Ret Time: 1.30 min (YMC ODS-A C18 S7, 3.0×50 mm, 2 min gradient (starting with 0% solvent B and ending with 70% solvent B), 5 mL/min.

EXAMPLE 122

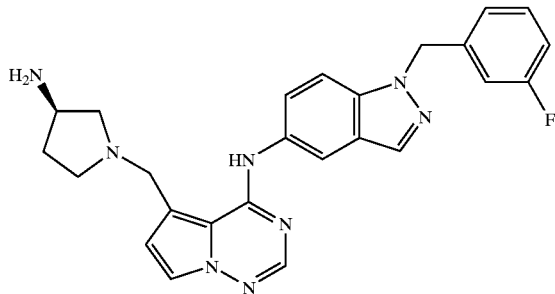

{5-[(3R)-3-Amino-pyrrolidin-1-ylmethy]-pyrrolo[2,1-f][1,2,4]triazin-4-yl}-[1-(3-fluoro-benzyl)-1H-indazol-5-yl]-amine A mixture of (5-benzenesulfinylmethyl-pyrrolo[2,1-f][1,2,4]triazin-4-yl)-[1-(3-fluoro-benzyl)-1H-indazol-5-yl]-amine (100 mg, 0.20 mmole) and (3R)-3-(N-tert-butoxycarbonylamino)pyrrolidine; (380 mg, 10 equiv) in a sealed tube was heated at 130° C. for 35 hr. The reaction mixture was taken up in DCM, washed water and dried (Na₂SO₄). After removal of the solvent the residue was taken up in DCM (1.5 mL) and TFA (1 mL) was added. The solvents were removed and the residue was dissolved in DCM, washed with water, and dried (Na₂SO₄). Removal of the solvent followed by radial chromatography (2 mm silica gel plate employing gradient elution with DCM containing 1 to 5% MeOH) to afforded the title compound as an oil (13 mg, 14%). $^1$H NMR (CDCl₃) δ 1.49 (br s, 2H), 1.66 (m, 1H), 2.29 (m, 1H), 2.43 (m, 1H), 3.69 (m, 1H), 3.87 (d, 1H, J=13.5 Hz), 3.96 (d, 1H, J=13.5 Hz), 5.58 (s, 2H), 6.49 (d, 1H, J=3 Hz), 6.8–7.6 (m, 7H), 7.92 (s, 1H), 8.04 (s, 1H), 8.26 (d, 1H, J=2 Hz); MS: 457 (M+H)⁺; HPLC Ret Time: 1.15 min (YMC Xterra ODS S7 C18, 3.0×50 mm column, 2 min gradient, 5 mL/min).

EXAMPLES 123 to 127

The follow examples were prepared in the same manner as Example 122.

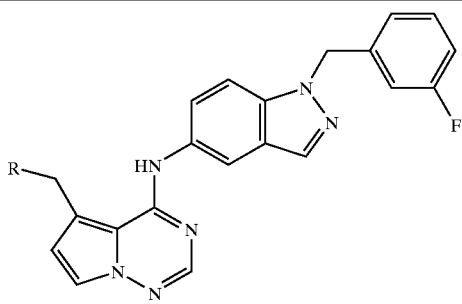

| Ex. | R | Compound Name | HPLC Ret Time (min) |
|---|---|---|---|
| 123 | H₂N-piperidinyl | [5-(4-Amino-piperidin-1-ylmethyl)-pyrrolo[2,1-f][1,2,4]triazin-4-yl]-[1-(3-fluoro-benzyl)-1H-indazol-5-yl]-amine | 1.03 |
| 124 | HN-piperidinyl-NH | [1-(3-Fluoro-benzyl)-1H-indazol-5-yl]-[5-(piperidin-4-ylaminomethyl)-pyrrolo[2,1-f][1,2,4]triazin-4-yl]-amine | 0.98 |
| 125 | H₂N-pyrrolidinyl | [5-((3R)-3-Amino-pyrrolidin-1-ylmethyl)-pyrrolo[2,1-f][1,2,4]triazin-4-yl]-[1-(3-fluoro-benzyl)-1H-indazol-5-yl]-amine | 1.15* |
| 126 | HN-piperidinyl-NH | (±)-[1-(3-Fluoro-benzyl)-1H-indazol-5-yl]-[5-(piperidin-3-ylaminomethyl)-pyrrolo[2,1-f][1,2,4]triazin-4-yl]-amine | 0.97* |
| 127 | H₂N-CH₂-piperidinyl | [5-(4-Aminomethyl-piperidin-1ylmethyl)-pyrrolo[2,1-f][1,2,4]triazin-4-yl]-[1-(3-fluoro-benzyl)-1H-indazol-5-yl]-amine | 1.53** |

Unless otherwise indicated, HPLC Retention Times were determined using a YMC S7 C18 3.0 × 50 mm column with a 2 minute gradient time and a flow rate of 5 mL/min. HPLC Retention Times marked with a "*" were determined using a YMC S7 C18 3.0 × 50 mm column with a 2 minute gradient time and a flow rate of 5 mL/min; with a "**" were determined using using a YMC ODS-A C18 S7 3.0 × 50 mm column with a 3 minute gradient time and a flow rate of 4 mL/min.

EXAMPLE 128

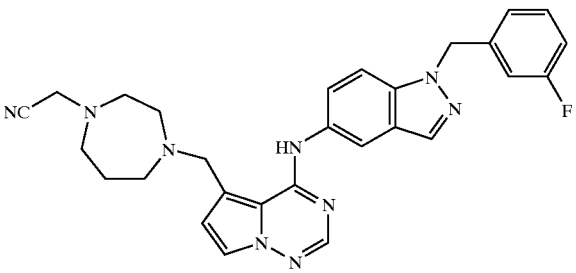

[1-(3-Fluoro-benzyl)-1H-indazol-5-yl]-[5-(4-cyanomethyl-[1,4]diazepan-1-ylmethyl)-pyrrolo[2,1-f][1,2,4]triazin-4-yl]-amine Bromoacetonitrile (0.028 mL, 4 equiv) was added to an ice cooled solution of 5-[1,4]diazepan-1-ylmethyl-pyrrolo[2,1-f][1,2,4]triazin-4-yl)-[1-(3-fluoro-benzyl)-1H-indazol-5yl]-amine (47 mg, 0.10 mmole) and TEA (0.055 mL, 4 equiv) in DCM (3 mL). This was left stirring for 1 hr and then removed from the ice bath. After standing overnight, the reaction was diluted with DCM, washed with water, and dried (Na₂SO₄). Removal of the solvent followed by radial chromatography (2 mm silica gel plate employing gradient elution with DCM containing 0 to 1% MeOH) afforded the title compound as an oil (49 mg, 95%). MS: 510 (M+H)⁺; HPLC Ret Time: 1.17 min (YMC S7 C18, 3.0×50 mm column, 2 min gradient, 5 mL/min).

EXAMPLE 129

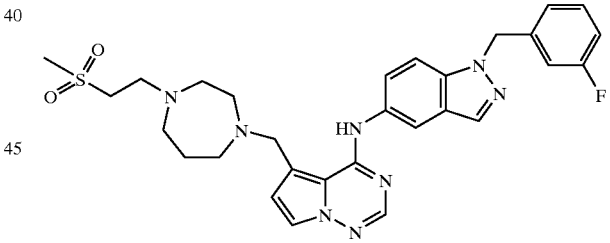

[1-(3-Fluoro-benzyl)-1H-indazol-5-yl]-{5-[4-(2-methanesulfonyl-ethyl)-[1,4]diazepan-1-ylmethyl]-pyrrolo[2,1-f][1,2,4]triazin-4-yl}-amine Methyl vinyl sulfone (0.042 mL, 4 equiv) was added to a solution of 5-[1,4]diazepan-1-ylmethyl-pyrrolo[2,1-f][1,2,4]triazin-4-yl)-[1-(3-fluoro-benzyl)-1H-indazol-5-yl]-amine (47 mg, 0.10 mmole) in DCM (3 mL). After stirring overnight, the solvent was removed and purification by radial chromatography (2 mm silica gel plate employing gradient elution with DCM containing 0 to 1% MeOH) afforded the title compound as an oil (54 mg, 93%).); MS: 577 (M+H)⁺; HPLC Ret Time: 1.08 min (YMC S7 C18, 3.0×50 mm column, 2 mm gradient, 5 mL/min).

EXAMPLE 130

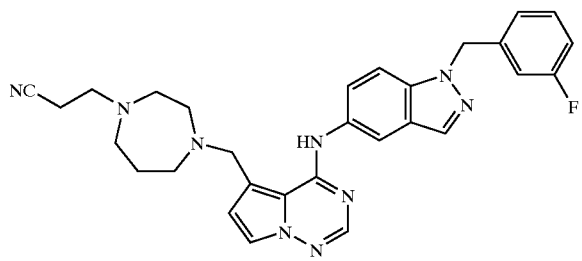

[1-(3-Fluoro-benzyl)-1H-indazol-5-yl]-{5-[4-(2-cyano-ethyl)-[1,4]diazepan-1-ylmethyl]-pyrrolo[2,1-f][1,2,4]triazin-4-yl}-amine Acrylonitrile (0.302 mL, 45 equiv) was added in 3 portions over 2 days to a solution of 5-[1,4]diazepan-1-ylmethyl-pyrrolo[2,1-f][1,2,4]triazin-4-yl)-[1-(3-fluoro-benzyl)-1H-indazol-5-yl-amine (47 mg, 0.10 mmole) in DCM (3 mL) at RT. The solvent was removed and purification by radial chromatography (2 mm silica gel plate employing gradient elution with DCM containing 0 to 1% MeOH) afforded the title compound as an oil (34 mg, 64%).); MS: 524 (M+H)$^+$; HPLC Ret Time: 1.08 min (YMC S7 C18, 3.0×50 mm column, 2 min gradient, 5 mL/min).

EXAMPLE 131

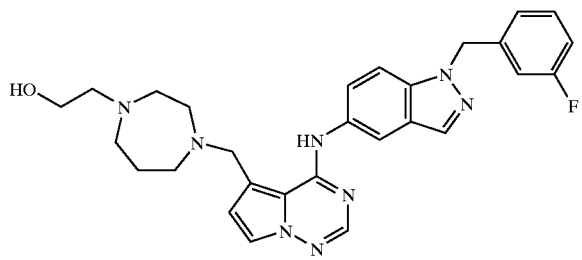

2-(4-{4-[1-(3-Fluoro-benzyl)-1H-indazol-5-ylamino]-pyrrolo[2,1-f][1,2,4]triazin-5-ylmethyl}-[1,4]diazepan-1-yl)ethanol A mixture of 5-[1,4]diazepan-1-ylmethyl-pyrrolo[2,1-f][1,2,4]triazin-4-yl)-[1-(3-fluoro-benzyl)-1H-indazol-5-yl]-amine (47 mg, 0.10 mmole), 2-bromoethanol (0.019 mL, 1.5 equiv) and K$_2$CO$_3$ (35 mg, 2.5 equiv) in CH$_3$CN (2.5 mL) was heated at reflux overnight. The reaction was then diluted with DCM, washed with water and dried (Na$_2$SO$_4$). The solvent was removed and purification by radial chromatography (2 mm silica gel plate employing gradient elution with DCM containing 0 to 5% MeOH) afforded the title compound as an oil (21 mg, 41%). MS: 515 (M+H)$^+$; HPLC Ret Time: 1.15 min (YMC Xterra ODS S7 C18, 3.0×50 mm column, 2 min gradient, 5 mL/min).

EXAMPLE 132

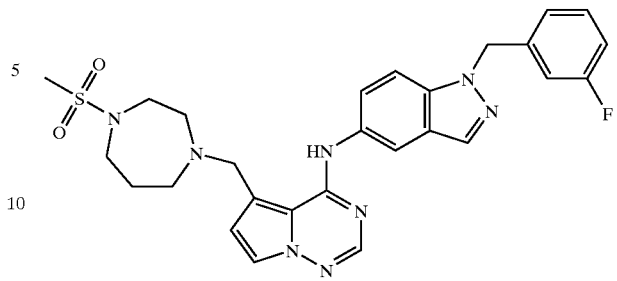

[1-(3-Fluoro-benzyl)-1H-indazol-5-yl]-[5-(4-methanesulfonyl-[1,4]diazepan-1-ylmethyl)-pyrrolo[2,1-f][1,2,4]triazin-4-yl]-amine Methanesulfonyl chloride (0.034 mL, 4 equiv) was added to an ice an ice cooled solution of 5-[1,4]diazepan-1-ylmethyl-pyrrolo[2,1-f][1,2,4]triazin-4-yl)-[1-(3-fluoro-benzyl)-1H-indazol-5-yl]-amine (35 mg, 0.074 mmole) and TEA (0.041 mL, 4 equiv) in DCM (2.5 mL). This was left stirring for 1 hr and then removed from the ice bath. After standing overnight, the reaction was diluted with DCM, washed with water, and dried (Na$_2$SO$_4$). Removal of the solvent followed by radial chromatography (2 mm silica gel plate employing gradient elution with DCM containing 0 to 2% MeOH) afforded the title compound as an oil (22 mg, 54%).); MS: 549 (M+H)$^+$; HPLC Ret Time: 1.26 min (YMC Xterra ODS S7 C18, 3.0×50 mm column, 2 min gradient, 5 mL/min).

EXAMPLE 133

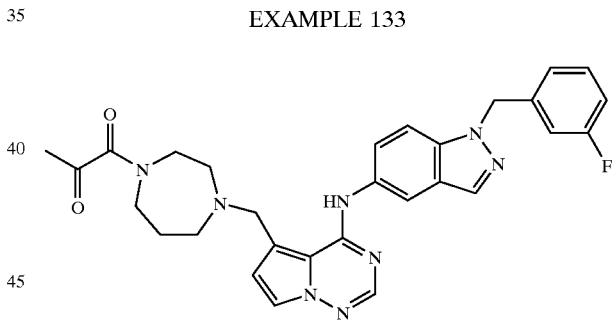

1-(4-{4-[1-(3-Fluoro-benzyl)-1H-indazol-5-ylamino]-pyrrolo[2,1-f][1,2,4]triazin-5-ylmethyl}-[1,4]diazepan-1-yl)-propane-1,2-dione A solution of pyruvic acid (0.008 mL, 1 equiv) and 5-[1,4]diazepan-1-ylmethyl-pyrrolo[2,1-f][2,1-f][1,2,4]triazin-4-yl)-[1-(3-fluoro-benzyl)-1H-indazol-5-yl]-amine (47 mg, 0.10 mmole) in EtOAc (3 mL) was cooled to −16° C. and a solution of dicyclohexylcarbodiimide (22 mg, 1.1 equiv) in EtOAc (0.5 mL) was added. This was allowed to slowly warm to RT and was left stirring overnight. The reaction was filtered and the solvent was removed from the filtrate. Radial chromatography of the residue (2 mm silica gel plate employing gradient elution with DCM containing 0 to 2% MeOH) afforded the title compound as an oil (8 mg, 14%). MS: 541 (M+H)$^+$; HPLC Ret Time: 1.27 min (YMC Xterra ODS S7 C18, 3.0×50 mm column, 2 min gradient, 5 mL/min).

What is claimed is:

1. A compound of formula I

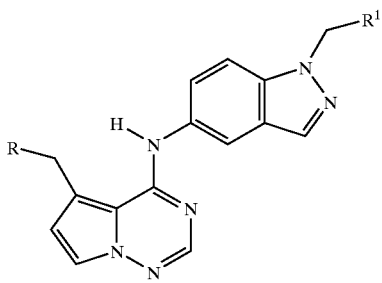

its enantiomers, diastereomers, or pharmaceutically acceptable salts, or solvates thereof, wherein R is selected from the group consisting of $SR^2$, $SOR^2$, $SO_2R^2$, $OR^2$, and $NR^3R^4$;

$R^1$ is selected from the group consisting of aryl, substituted aryl, heterocyclo, and substituted heterocyclo;

$R^2$ is selected from the group consisting of hydrogen, alkyl, substituted alkyl, aryl, substituted aryl, aralkyl, heterocyclo, and substituted heterocyclo;

$R^3$ and $R^4$ are independently selected from the group consisting of hydrogen, alkyl, substituted alkyl, aryl, substituted aryl, heterocyclo, and substituted heterocyclo; or $R^3$ and $R^4$ may together form an optionally substituted monocyclic 4–8 membered saturated or unsaturated carbocyclic or heterocyclic ring, or an optionally substituted bicyclic 7 to 12 membered saturated or unsaturated carbocyclic or heterocyclic ring.

2. The compound according to claim 1 wherein $R^1$ is selected from the group consisting of benzene, fluoro substituted benzene and pyridine.

3. The compound according to claim 2 wherein $R^1$ is a fluoro substituted benzene.

4. The compound according to claim 3 wherein R is an ether.

5. The compound according to claim 1 selected from the group consisting of:

(5-[1,4]Diazepan-1-ylmethyl-pyrrolo[2,1-f][1,2,4]triazin-4-yl)-[1-(3-fluoro-benzyl)-1H-indazol-5-yl]-amine;

[1-(3-Fluoro-benzyl)-1H-indazol-5-yl]-(5-imidazol-1-ylmethyl-pyrrolo[2,1-f][1,2,4]triazin-4-yl)-amine;

1-{4-[1-(3-Fluoro-benzyl)-1H-indazol-5-ylamino]-pyrrolo[2,1-f][1,2,4]triazin-5-ylmethyl}-piperidine-3-carboxylic acid amide;

[1-(3-Fluoro-benzyl)-1H-indazol-5-yl]-[5-(4-methyl-piperazin-1-ylmethyl)-pyrrolo[2,1-f][1,2,4]triazin-4-yl]-amine;

2-(4-{4-[1-(3-Fluoro-benzyl)-1H-indazol-5-ylamino]-pyrrolo[2,1-f][1,2,4]triazin-5-ylmethyl}-piperazin-1-yl)-ethanol;

1-{4-[1-(3-Fluoro-benzyl)-1H-indazol-5-ylamino]-pyrrolo[2,1f][1,2,4]triazin-5-ylmethyl}-(3R)-pyrrolidin-3-ol;

(1-{4-[1-(3-Fluoro-benzyl)-1H-indazol-5-ylamino]-pyrrolo[2,1-f][1,2,4]triazin-5-ylmethyl}-piperidin-4-yl)-methanol;

1-{4-[1-(3-Fluoro-benzyl)-1H-indazol-5-ylamino]-pyrrolo[2,1-f][1,2,4]triazin-5-ylmethyl}-piperidin-4-ol;

(2R)-3-({4-[1-(3-Fluoro-benzyl)-1H-indazol-5-ylamino]-pyrrolo[2,1-f][1,2,4]triazin-5-ylmethyl}-amino)-propane-1,2-diol;

2-({4-[1-(3-Fluoro-benzyl)-1H-indazol-5-ylamino]-pyrrolo[2,1-f][1,2,4]triazin-5-ylmethyl}-amino)-ethanol;

1-{4-[1-(3-Fluoro-benzyl)-1H-indazol-5-ylamino]-pyrrolo[2,1-f][1,2,4]triazin-5-ylmethyl}-(3S)-pyrrolidin-3-ol;

[1-(3-Fluoro-benzyl)-1H-indazol-5-yl]-[5-(4-cyanomethyl-cyclohexylmethyl)-pyrrolo[2,1-f][1,2,4]triazin-4-yl]-amine;

[5-(3,5-Dimethyl-piperazin-1-ylmethyl)-pyrrolo[2,1-f][1,2,4]triazin-4-yl]-[1-(3-fluoro-benzyl)-1H-indazol-5-yl]-amine;

[1-(3-Fluoro-benzyl)-1H-indazol-5-yl]-[5-((3S)-3-methyl-piperazin-1-ylmethyl)-pyrrolo[2,1-f][1,2,4]triazin-4-yl]-amine;

4-{4-[1-(3-Fluoro-benzyl)-1H-indazol-5-ylamino]-pyrrolo[2,1-f][1,2,4]triazin-5-ylmethyl}-piperazine-2-carboxylic acid amide;

4-{4-[1-(3-Fluoro-benzyl)-1H-indazol-5-ylamino]-pyrrolo[2,1-f][1,2,4]triazin-5-ylmethyl}-piperazin-2-one;

2-({4-[1-(3-Fluoro-benzyl)-1H-indazol-5-ylamino]-pyrrolo[2,1-f][1,2,4]triazin-5-ylmethyl}-amino)-2-methyl-propane-1,3-diol;

2-({4-[1-(3-Fluoro-benzyl)-1H-indazol-5-ylamino]-pyrrolo[2,1-f][1,2,4]triazin-5-ylmethyl}-amino)-propane-1,3-diol;

[1-(3-Fluoro-benzyl)-1H-indazol-5-yl]-(5-piperazin-1-ylmethyl-pyrrolo[2,1-f][1,2,4]triazin-4-yl)amine;

[1-(3-Fluoro-benzyl)-1H-indazol-5-yl]-{5-[4-(2-methoxy-ethylamino)-piperidin-1-ylmethyl]-pyrrolo[2,1-f][1,2,4]triazin-4-yl}-amine;

1-{4-[1-(3-Fluoro-benzyl)-1H-indazol-5-ylamino]-pyrrolo[2,1-f][1,2,4]triazin-5-ylmethyl}-[1,4]diazepan-5-one;

[5-(4-Amino-piperidin-1-ylmethyl)-pyrrolo[2,1-f][1,2,4]triazin-4-yl]-[1-(3-fluoro-benzyl)-1H-indazol-5-yl]-amine;

(+)-[5-(cis-4-Amino-3-methyl-piperidin-1-ylmethyl)-pyrrolo[2,1-f][1,2,4]triazin-4-yl]-[1-(3-fluoro-benzyl)-1H-indazol-5-yl]-amine;

(+)-[5-(trans-4-Amino-3-methyl-piperidin-1-ylmethyl)-pyrrolo[2,1-f][1,2,4]triazin-4-yl]-[1-(3-fluoro-benzyl)-1H-indazol-5-yl]-amine;

1-{4-[1-(3-Fluoro-benzyl)-1H-indazol-5-ylamino]-pyrrolo[2,1-f][1,2,4]triazin-5-ylmethyl}-piperidin-4-one;

(1-{4-[1-(3-Fluoro-benzyl)-1H-indazol-5-ylamino]-pyrrolo[2,1-f][1,2,4]triazin-5-ylmethyl}-(+)-[1,4]diazepan-6-ol;

1-{4-[1-(3-Fluoro-benzyl)-1H-indazol-5-ylamino]-pyrrolo[2,1-f][1,2,4]triazin-5-ylmethyl}-(6R)-[1,4]diazepan-6-ol;

2-(1-{4-[1-(3-Fluoro-benzyl)-1H-indazol-5-ylamino]-pyrrolo[2,1-f][1,2,4]triazin-ylmethyl}-piperidin-4-ylamino)-ethanol;

[1-(3-Fluoro-benzyl)-1H-indazol-5-yl]-[5-(4-methylamino-piperidin-1-ylmethyl)-pyrrolo[2,1-f][1,2,4]triazin-4-yl]-amine;

[5-(6,6-Difluoro-[1,4]diazepan-1-ylmethyl)-pyrrolo[2,1-f][1,2,4]triazin-4-yl]-[1-(3-fluoro-benzyl)-1H-indazol-5-yl]-amine;

(+)-[1-(3-Fluoro-benzyl)-1H-indazol-5-yl]-[5-(6-fluoro-[1,4]diazepan-1-ylmethyl)-pyrrolo[2,1-f][1,2,4]triazin-4-yl]-amine;

1-{4-[1-(3Fluoro-benzyl)-1H-indazol-5-ylamino]-pyrrolo[2,1-f][1,2,4]triazin-5-ylmethyl}-[1,4]diazepan-6-one;

[1-(3-Fluoro-benzyl)-1H-indazol-5-yl]-[5-(piperidin-4-yloxymethyl)-pyrrolo[2,1-f][1,2,4]triazin-4-yl]-amine;

2-{4-[1-(3-Fluoro-benzyl)-1H-indazol-5-ylamino]-pyrrolo[2,1-f][1,2,4]triazin-5-ylmethoxy}-ethanol;

[1-(3-Fluoro-benzyl)-1H-indazol-5-yl]-[5-(piperidin-3-ylmethoxymethyl)-pyrrolo[2,1-f][1,2,4]triazin-4-yl]-amine;

3-{4-[1-(3-Fluoro-benzyl)-1H-indazol-5-ylamino]-pyrrolo[2,1-f][1,2,4]triazin-5-ylmethoxy}-propane-1,2-diol;

[5-(4-Amino-butoxymethyl)-pyrrolo[2,1-f][1,2,4]triazin-4-yl]-[1-(3-fluoro-benzyl)-1H-indazol-5-yl]-amine;

[5-(4-Amino-propoxymethyl)-pyrrolo[2,1-f][1,2,4]triazin-4-yl]-[1-(3-fluoro-benzyl)-1H-indazol-5-yl]-amine;

([1-(3-Fluoro-benzyl)-1H-indazol-5-yl]-[5-({2S}-morpholin-2-ylmethoxymethyl)-pyrrolo[2,1-f][1,2,4]triazin-4-yl]-amine;

[trans-5-(4-Amino-cyclohexyloxymethyl)-pyrrolo[2,1-f][1,2,4]triazin-4-yl]-[1-(3-fluoro-benzyl)-1H-indazol-5-yl]-amine;

[5-(2-Amino-ethoxymethyl)-pyrrolo[2,1-f][1,2,4]triazin-4-yl]-[1-(3-fluoro-benzyl)-1H-indazol-5-yl]-amine;

3-{4-[1-(3-Fluoro-benzyl)-1H-indazol-5-ylamino]-pyrrolo[2,1-f][1,2,4]triazin-5-ylmethoxy}-propan-1-ol;

{5-[(3R)-3-Amino-pyrrolidin-1-ylmethy]-pyrrolo[2,1-f][1,2,4]triazin-4-yl}-[1-(3-fluoro-benzyl)-1H-indazol-5-yl]-amine;

[5-(4-Amino-piperidin-1-ylmethyl)-pyrrolo[2,1-f][1,2,4]triazin-4-yl]-[1-(3-fluoro-benzyl)-1H-indazol-5-yl]-amine;

[1-(3-Fluoro-benzyl)-1H-indazol-5-yl]-[5-(piperidin-4-ylaminomethyl)-pyrrolo[2,1-f][1,2,4]triazin-4-yl]-amine;

(+)-[1-(3-Fluoro-benzyl)-1H-indazol-5-yl]-[5-(piperidin-3-ylaminomethyl)-pyrrolo[2,1-f][1,2,4]triazin-4-yl]-amine;

[5-(4-Aminomethyl-piperidin-1ylmethyl)-pyrrolo[2,1-f][1,2,4]triazin-4-yl]-[1-(3-fluoro-benzyl)-1H-indazol-5-yl]-amine; and 2-(4-{4-[1-(3-Fluoro-benzyl)-1H-indazol-5-ylamino]-pyrrolo[2,1-f][1,2,4]triazin-5-ylmethyl}-[1,4]diazepan-1-yl)-ethanol.

6. A pharmaceutical composition comprising a compound of claim 1 and a pharmaceutically acceptable carrier.

7. A pharmaceutical composition comprising a compound of claim 1 in combination with a pharmaceutically acceptable carrier and at least one other anti-cancer or cytotoxic agent formulated as a fixed dose.

8. The pharmaceutical composition of claim 7 wherein said anti-cancer or cytotoxic agent is selected from the group consisting of: tamoxifen, toremifen, raloxifene, droloxifene, iodoxifene, megestrol acetate, anastrozole, letrazole, borazole, exemestane; flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan and an epothilone.

9. A method for treating a proliferative disease, selected from the group consisting of psoriasis and rheumatoid arthritis, comprising administering to a warm-blooded species in need thereof, a therapeutically effective amount of a compound of claim 1.

* * * * *